(12) United States Patent
Molnar et al.

(10) Patent No.: US 10,933,234 B2
(45) Date of Patent: Mar. 2, 2021

(54) SYSTEM, DEVICES, AND METHODS COMBINING SPINAL STABILIZATION AND NEUROMODULATION

(71) Applicant: SynerFuse, Inc., Minneapolis, MN (US)

(72) Inventors: Gregory F. Molnar, Blaine, MN (US); Harry Puryear, Shoreview, MN (US); Nazmi Peyman, Glen Allen, VA (US); Justin D. Zenanko, Minneapolis, MN (US)

(73) Assignee: SynerFuse, Inc., Minneapolis, MN (US)

( * ) Notice: Subject to any disclaimer, the term of this patent is extended or adjusted under 35 U.S.C. 154(b) by 53 days.

(21) Appl. No.: 16/409,616

(22) Filed: May 10, 2019

(65) Prior Publication Data
US 2019/0344070 A1 Nov. 14, 2019

Related U.S. Application Data

(60) Provisional application No. 62/670,034, filed on May 11, 2018.

(51) Int. Cl.
*A61B 17/70* (2006.01)
*A61N 1/05* (2006.01)

(52) U.S. Cl.
CPC ........ *A61N 1/0558* (2013.01); *A61B 17/7034* (2013.01); *A61N 1/0553* (2013.01)

(58) Field of Classification Search
CPC .. A61N 1/0558; A61N 1/0553; A61N 1/0452; A61N 1/36071; A61N 1/40;
(Continued)

(56) References Cited

U.S. PATENT DOCUMENTS

| 8,523,930 B2* | 9/2013 | Saunders | A61B 17/7037 607/105 |
| 9,259,248 B2* | 2/2016 | Leuthardt | A61B 17/80 |

(Continued)

OTHER PUBLICATIONS

Inntemational Preliminary Report on Patentability issued in related PCT application No. PCT/US2019/031865, dated Nov. 26, 2020.
(Continued)

*Primary Examiner* — Pedro Philogene
(74) *Attorney, Agent, or Firm* — Barnes & Thornburg LLP; Jeffrey R. Stone

(57) ABSTRACT

A pain management system includes a spinal stabilization device and a neuromodulation device. The spinal stabilization device includes a rod, a plurality of pedicle screws each having a screw-head defining a screw-head cavity configured to receive a portion of the rod, and a corresponding plurality of inserts configured to engage with the inner wall of the cavity to secure the rod in place in the cavity. The neuromodulation device includes a therapy module comprising electronics packaged within a housing. The housing has a form factor having at least one feature configured to mate with a corresponding feature of the screw-head of one of the plurality of pedicle screws. The respective features mate in a manner that enables the therapy module to mechanically couple to and subsequently decouple from the screw-head of the pedicle screw.

11 Claims, 15 Drawing Sheets

(58) Field of Classification Search
CPC .. A61N 1/08; A61N 1/36057; A61N 1/37223;
A61N 1/403; A61N 1/36135; A61N
1/37518; A61N 1/36062; A61N 1/0551;
A61N 1/3787; A61N 1/3605; A61B
17/7034; A61B 17/7061; A61B 17/7062;
A61B 17/7043; A61B 17/7002; A61B
17/7049; A61B 17/7074; A61B 17/7001;
A61B 2017/00022; A61B 2017/00075;
A61B 2017/00084; A61B 2017/00734;
A61B 2017/564; A61B 5/4851; A61B
5/4824; A61B 5/06; A61B 5/0031; A61B
5/686; A61B 5/076; A61F 2/4405; A61F
2/44
USPC ........................................................ 606/265
See application file for complete search history.

(56) References Cited

U.S. PATENT DOCUMENTS

| 10,456,187 B2* | 10/2019 | Edidin .................. A61B 18/04 |
| 2007/0150034 A1 | 6/2007 | Rooney et al. |
| 2013/0317585 A1* | 11/2013 | Barker ................. A61N 1/0558 |
| | | 607/117 |
| 2017/0291026 A1* | 10/2017 | Imran .................. A61N 1/0553 |
| 2017/0333702 A1 | 11/2017 | Barner |

OTHER PUBLICATIONS

International Search Report and Written Opinion issued in related PCT application No. PCT/US2019/031865, dated Dec. 3, 2019.

\* cited by examiner

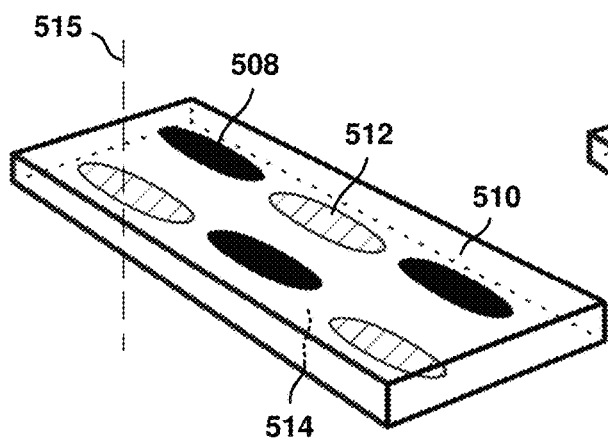
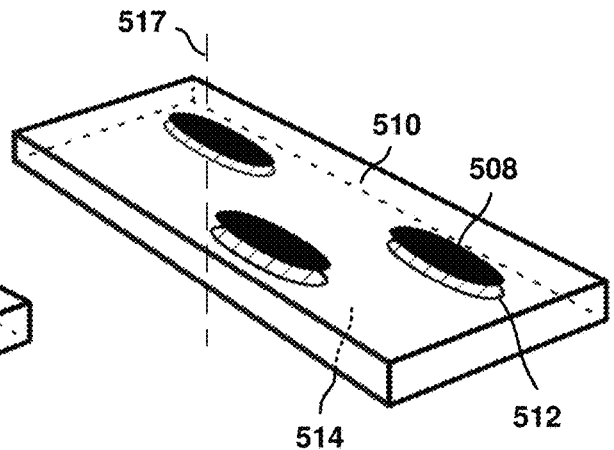
FIG. 5E            FIG. 5F
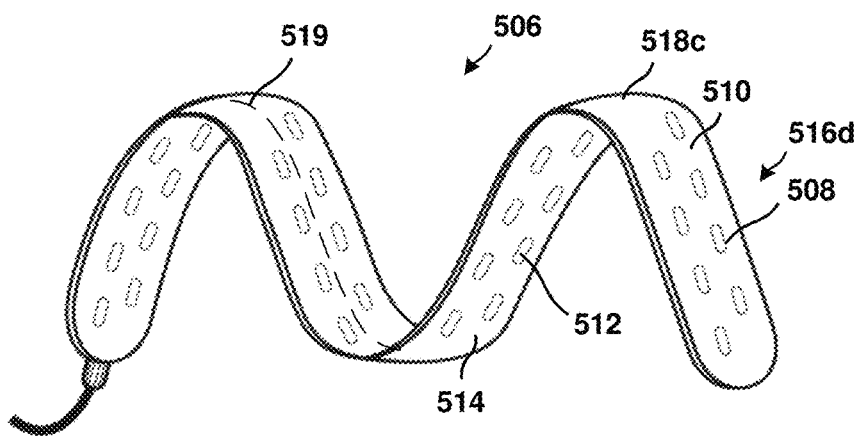
FIG. 5G
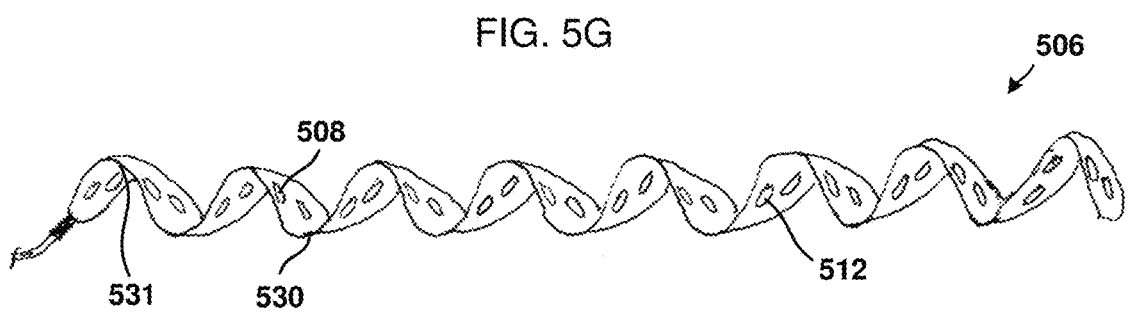
FIG. 5H
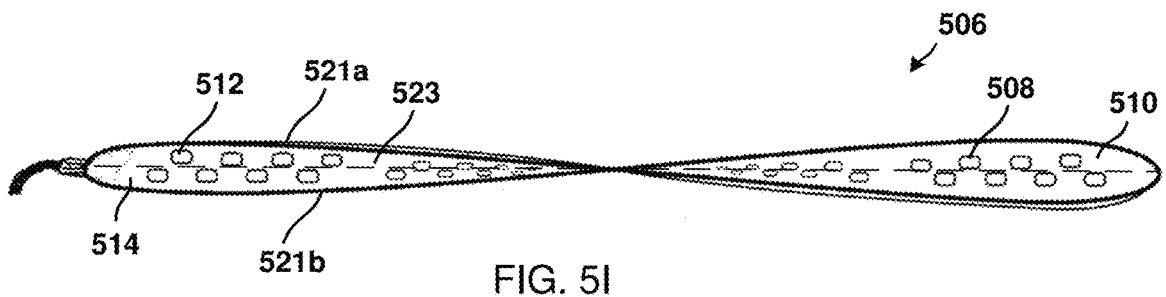
FIG. 5I

SYSTEM, DEVICES, AND METHODS COMBINING SPINAL STABILIZATION AND NEUROMODULATION

CROSS-REFERENCE TO RELATED APPLICATION

This application claims the benefit of and priority to U.S. Provisional Patent Application Ser. No. 62/670,034, filed May 11, 2018, entitled "Method and Apparatus to Deliver Neuromodulation to the Spine", the entire disclosure of which is incorporated herein by reference.

TECHNICAL FIELD

The present disclosure relates generally to the treatment of chronic back pain, and more particularly, to systems, devices, and methods that treat chronic back pain through concurrent provision of spinal stabilization and neuromodulation.

BACKGROUND

Chronic lower back pain is caused by spinal instability that results from conditions such as degenerative disc disease, fractures, spinal stenosis, and spondylolisthesis (slippage of the bony vertebra). Typically, a patient suffering from chronic lower back pain is first treated using conservative pain management techniques, such as exercise, physical therapy, injections and medication. When conservative pain management does not effectively treat a patient's pain symptoms, a more aggressive pain management approach may be taken.

In a more aggressive pain management scenario, a patient may undergo a surgical spinal fusion procedure that utilizes a fixation device to immobilize and straighten the back to restore stability to the back and relieve pain. Spinal fusion is a surgical technique to stabilize the spinal column. Fusion surgery is designed to create solid bone between the adjoining vertebrae, eliminating any movement between the bones. The goal of the surgery is to address mechanical aspects of pain and/or neural compression or irritation as a cause of pain. Spinal fusion may be recommended for cases of spinal instability such as spondylolisthesis, degenerative disc disease or recurrent disc herniations, spinal infections (e.g. tuberculosis or pyogenic), fractures of spine and spinal tumors.

With reference to FIG. 1A, an example fixation device utilized for spinal fusion includes a pair of pedicle screws and a rod. During a spinal fusion surgical procedure, access to a space between adjacent vertebrae is gained, for example, through a laminotomy. A bone material, called a bone graft, is placed into the space to help promote the fusion of the vertebrae. After placement of the bone graft, the fixation device is implanted to stabilize the back during the time it takes for fusion to complete. To this end, the screw thread portion of each of the pedicle screws is screwed into a respective pedicle of a respective vertebrae, leaving the screw head portion exposed. A rigid and inflexible rod is then placed in and between the screw heads and secured in place by at each screw head by a screw-head nut. The rod-and-screw fixation device prevents relative movement between the adjacent vertebrae to which it is attached.

Spinal fusion, however, does not always relieve pain as intended. In fact, residual pain occurs after up to 40% of spinal surgeries, costing an average of $20 billion US health care dollars per year and severely reducing quality of life for patients. Residual pain after a traditional back surgery often leaves a patient seeking other aggressive pain-relieving therapies such as oral opioids, spinal injections, radiofrequency (RF) nerve ablation or spinal cord stimulation, or eventually pursuing another spinal surgery to relieve their pain. This condition, also referred to as failed back surgery syndrome, is one of the primary indications for traditional spinal cord stimulation.

Since spinal cord stimulation is well known to effectively treat chronic neuropathic pain it suggests that such neuropathic pain exists in patients with spinal instability. The genesis of neuropathic pain often arises as a result of direct damage and/or irritation to nerves and is different from the natural mechanical/nociceptive pain (i.e. telling us something is wrong in our body) that may also exist in combination with spinal instability. The neuropathic component of the pain may have arisen as a result of the patient's chronic instability and spinal nerve compression and/or irritation within the weakened/unstable spinal vertebrae at the spinal level affected prior to their surgery. Additional neuropathic pain can arise from the surgical cutting (skin, muscle, bones, nerves) to perform the surgery. So neuromodulation can treat this pre-existing neuropathic pain and it will also treat or even prevent any subsequent neuropathic pain that arises from the surgery.

With reference to FIG. 1B, an example spinal cord stimulation system utilized for treating chronic back pain includes a pulse generator and a pair of leads. During the implant procedure, the electrode-bearing ends of the leads are percutaneously implanted into the epidural space of the spine, to place the electrodes in the area of the nerves that are to be neuromodulated. The portion of the leads outside of the epidural space are then tunneled beneath the skin down to, and then connected to the pulse generator. The pulse generator is implanted in a subcutaneous pocket formed to a side of the spinal column.

Most patients, however, are not indicated for spinal cord stimulation until they have failed many other therapies, and it is often 2-5 years after their initial spinal fusion before spinal cord stimulation is offered, resulting in prolonged disability and morbidity. As a result, many patients do not experience adequate relief and often become reliant on addictive opioids in a futile attempt to reduce their remaining pain. This contributed to the 2.1 million people who had an opioid use disorder, 11.5 million people who abused prescription opioids in 2016 and the annual economic cost of the opioid crisis, estimated to be over $500 billion in 2015. Due to the extent of this public health epidemic, it remains critical to exhaust all other methods of pain management before turning to opioids, particularly since no clinical studies have confirmed the effectiveness of long-term opioid usage on chronic back pain.

It is therefore desirable to reduce or eliminate the separation in time between surgical spinal procedures and neurostimulation implant procedures to enable the provision of neuromodulation therapies as soon as possible after occurrence of a failed back surgery. It is also desirable to have a pain management system that combines spinal fixation hardware and neuromodulation components to thereby provide mechanical/nociceptive pain therapy concurrent with neuropathic pain therapy. The concepts disclosed below address these desires and others.

SUMMARY

An implantable medical lead for neuromodulating nerve structures includes a ribbon structure having a first side and a second side opposite the first side. A plurality of first electrodes are associated with the first side and arranged in a first pattern, while a plurality of second electrodes associated with the second side and arranged in a second pattern. The ribbon structure is configured to transition from a planar state to a non-planar state upon the application of a force and to remain in the non-planar state upon removal of the force. For example, the non-planar state may be an undulating state during which the ribbon structure bends in at least one curve or in a series of successive curves in alternating directions along the longitudinal axis of the ribbon structure. In one finer aspect of the lead, the undulating state comprises at least one curve having a radius of curvature in the range of 1 mm and 3 mm. In another example, the non-planar state may be a twisted state during which the edges of the ribbon structure along the length of the ribbon structure curve about the longitudinal axis of the ribbon structure. The ability of the ribbon structure to assume different non-planar states is a function of the configuration of the ribbon structure, including the material properties of the ribbon structure, the thickness of the ribbon structure, and the electrode size, interelectrode spacing and electrode patterns.

An implantable neuromodulation device for implant with a spinal stabilization device includes a therapy module and a lead. The spinal stabilization device includes a pair of pedicle screws, each having a screw-head with a screw-head cavity, and the therapy module includes a housing having a form factor comprising at least one feature configured to mate with a corresponding feature of a screw-head of one of the pedicle screws. The respective features mate in a manner that enables the therapy module to mechanically couple to and subsequently decouple from the screw-head of the pedicle screw. For example, the mating may be through threaded engagement or friction. The lead includes a distal-end region having a plurality of electrodes and a proximal-end region having a lead interface structure configured to mechanically and electrically couple to and subsequently decouple from the therapy module.

A pain management system includes a spinal stabilization device and a neuromodulation device. The spinal stabilization device includes a rod, a plurality of pedicle screws each having a screw-head defining a screw-head cavity configured to receive a portion of the rod, and a corresponding plurality of inserts configured to engage with the inner wall of the cavity to secure the rod in place in the cavity. The neuromodulation device includes a therapy module comprising electronics packaged within a housing. The housing has a form factor having at least one feature configured to mate with a corresponding feature of the screw-head of one of the plurality of pedicle screws. The respective features mate in a manner that enables the therapy module to mechanically couple to and subsequently decouple from the screw-head of the pedicle screw. The pain management system as such, simultaneously addresses three types of pain: (1) mechanical/nociceptive pain caused from poor alignment or instability, (2) neuropathic pain, caused by damage of the nerve trunk and over sensitization of nerves in the brain and spinal cord, and (3) post-surgical pain, which is inherently caused by the surgical procedure.

A method of treating chronic back pain includes stabilizing a pair of vertebrae of the back of a patient healing from spinal fusion and neuromodulating one or more nerve structures associated with the pair of vertebrae while the patient is healing from the spinal fusion. The stabilizing treats nociceptive pain resulting from misalignment of the vertebrae or compression of nerves between or adjacent the vertebrae, while the neuromodulating treats neuropathic pain resulting from damage of the nerve trunk and over sensation of nerves in the brain and spinal cord.

A method of implanting a pain management system having a spinal stabilization hardware and a neuromodulation device includes creating direct access to nerve structures while implanting the spinal stabilization hardware, and placing a lead on or adjacent to target nerve structures under direct visual access. The method further includes mechanically coupling a therapy module of the neuromodulation device to a component of the spinal stabilization hardware; and mechanically and electrically coupling a lead of the neuromodulation device to the therapy module.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of system, device, and methods will now be presented in the detailed description by way of example, and not by way of limitation, with reference to the accompanying drawings, which are not to scale, wherein:

FIG. 5E is an illustration of a portion of the ribbon structure of the ribbon lead of FIG. 5A where the electrodes on opposite sides are staggered or offset relative to each other.

FIG. 5F is an illustration of a portion of the ribbon structure of the ribbon lead of FIG. 5A where the electrodes on opposite sides are stacked or aligned relative to each other.

FIG. 5G is an illustration of the ribbon lead of FIG. 5A where the ribbon structure has been subjected to bending forces and has assumed an undulated configuration along its longitudinal axis.

FIG. 5H is an illustration of the ribbon lead of FIG. 5A where the ribbon structure has been subjected to bending forces and has assumed an undulated configuration along its longitudinal axis having sharper curves, e.g. lower radius of curvature, than the curves of FIG. 5G.

FIG. 5I is an illustration of the ribbon lead of FIG. 5A where the ribbon support has been subjected to twisting forces and has assumed a twisted configuration about its longitudinal axis.

DETAILED DESCRIPTION

Figure 1A:
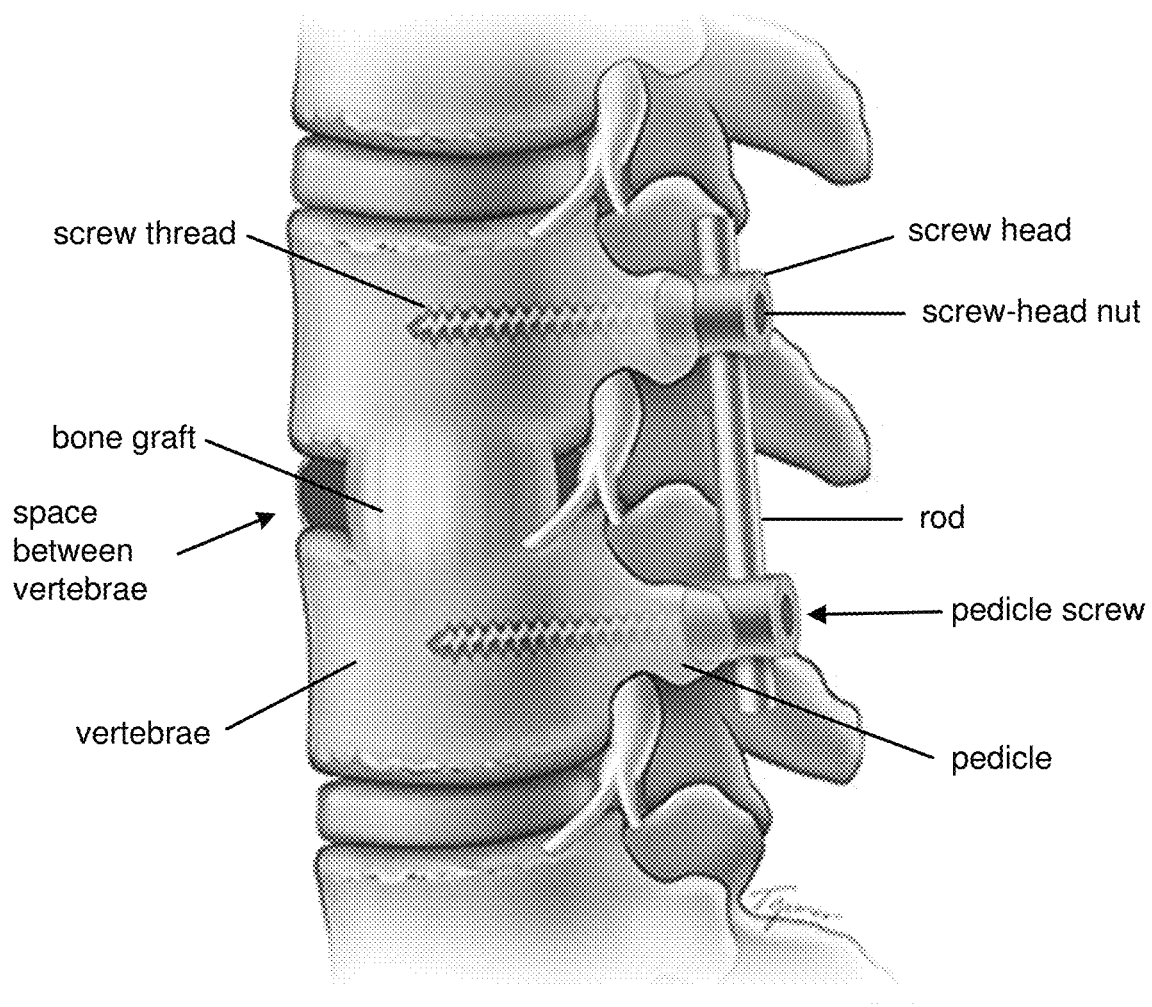
FIG. 1A is an illustration of an implanted spinal fixation device utilized for spinal fusion that includes a pair of pedicle screws and a rod.

Disclosed herein is an implantable pain management system that includes spinal stabilization hardware and a neuromodulation device having a therapy module component configured to mechanically couple to and subsequently decouple from a component of the spinal stabilization hardware. In one embodiment, the spinal stabilization hardware is in the form of a spinal fixation device that includes a pair of pedicle screws and a rod, and the therapy module is configured to mechanically coupled to and decoupled from a pedicle screw. The neuromodulation device also includes a lead having a ribbon like electrode-bearing region at its distal end and an interface structure at its proximal end that is configured to mechanically coupled to and decoupled from the therapy module. Given the coupling and decoupling capabilities of the therapy module and lead, the therapy module may be replaced if necessary by simply decoupling the lead from the therapy module and decoupling the therapy module from the pedicle screw.

The distal-end region of the ribbon lead includes a ribbon structure that is very flexible and is configured to transition from a substantially planar shape to a non-planar shape upon the application of a force and to remain in the non-planar state upon removal of the force. This allows the ribbon structure to assume and retain various shapes, including a shape that undulates along the length of the distal-end region or a shape that twists along the length of the distal-end region. Configured as such, the distal-end region of the lead is able to weave around and between spinal nerve structures and branches and to assume shapes that conform to the anatomy. Furthermore, electrodes may be located on each side of the distal-end region. This is advantageous in that if the distal-end region of the lead were to flip such that electrodes on one side of the region were no longer properly positioned to deliver stimulation energy to a nerve structure, the electrodes on the opposite side would be properly positioned and could serve as stimulating electrodes.

Also disclosed herein is a method of treating chronic back pain that includes simultaneously stabilizing vertebrae of the back during spinal fusion to treat nociceptive pain resulting from misalignment of the vertebrae or compression of nerves between or adjacent the vertebrae, and neuromodulating one or more nerve structures associated with the vertebrae to treat neuropathic pain resulting from damage of the nerve trunk and over sensation of nerves in the brain and spinal cord. Delivering neuromodulation at the same time as a spinal stabilization allows for a more effective and holistic treatment of a patient's pain ensuring better outcomes. The method disclosed herein allows for the two complementary therapies of spinal stabilization and neuromodulation to be delivered at the same time within the same anatomical space. The synergistic use of mechanical stabilization with neurostimulation might also contribute to relieving the acute pain associated with the spine surgery.

Also disclosed herein is a method of implanting a pain management system that includes spinal stabilization hardware and a neuromodulation device having a therapy module component configured to mechanically couple to and decouple from a component of the spinal stabilization hardware. Spinal stabilization hardware is implanted as part of a spinal fusion procedure. As part of this surgical procedure, open access to nerve structures in the area of the fusion is provided and a lead of a neuromodulation device is placed at or near the nerve structures. Subsequently, the therapy module is mechanically coupled to a component of the spinal stabilization hardware and the lead is mechanically and electrically coupled to the therapy module.

Regarding lead placement, because the spine is exposed during the spinal fusion procedure, some nerve structures and branches may be directly visible to the spine surgeon. This enables direct placement of the lead by the surgeon without the need for implant tools such as catheters or sheaths. For example, using a transforaminal approach, the distal-end of the ribbon lead may weave through and around nerve structures, including for example, ventral roots, dorsal roots, dorsal root ganglia (DRG) and the spinal cord. Stimulation could also be delivered to other aspects of the spinal nerve from more peripheral rami branches or more central to the dorsal root entry zone (DREZ) or spinal thalamic tract. Multiple nerve levels could be targeted bilaterally to cover the patient's painful dermatomes during the spine surgery with easy surgical access and anatomical visibility.

Figure 1B:
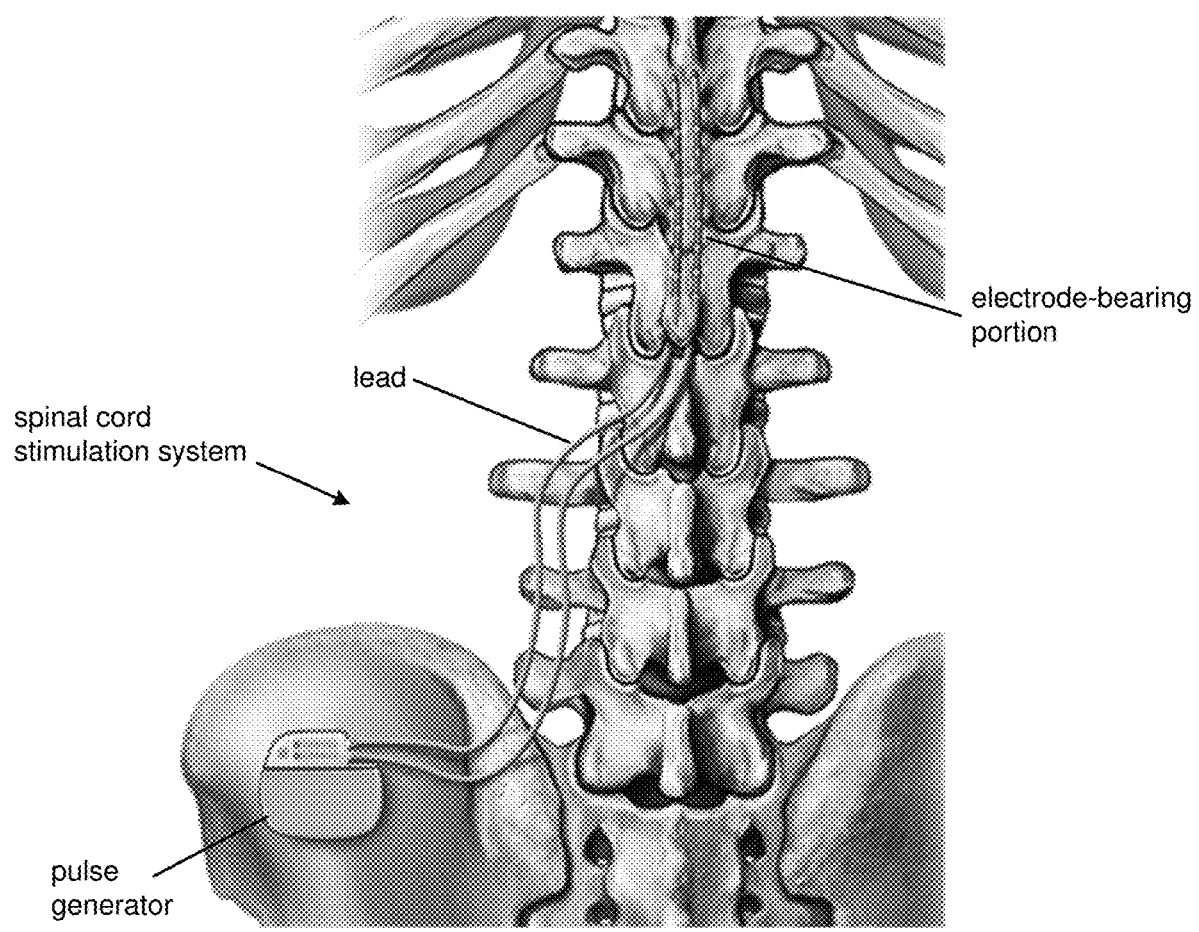
FIG. 1B is an illustration of an implanted spinal cord stimulation system utilized for treating chronic back pain that includes a pulse generator and a pair of leads.

In some cases, spinal fusion is prescribed separately from neuromodulation, with spinal fusion typically being prescribed first in time, with neuromodulation being delayed until other treatment options are exhausted. The time between a spinal fusion procedure and a neuromodulation device implant procedure in these cases may be 6-10 years. It can also be 20 or more years due to lack of awareness or specialist referral access, opioid issues, etc. In other cases, however, a patient may be prescribed both spinal fusion and neuromodulation. Traditionally, however, the neuromodulation device implant procedure and the spinal fusion procedure are performed separately for any of several reasons. For example, implantation of a traditional neuromodulation device, such as shown in FIG. 1B, may fall outside the spine surgeon's traditional practice, thus requiring the patient to be referred to a pain specialist that implants neuromodulation devices. Thus, even in the rare case of concurrent prescription of the spinal fusion and neuromodulation, the time between a spinal fusion procedure and a neuromodulation device implant procedure may range between 3 months to 1 year. Given such separations in time, during later implantation of a neuromodulation device it is often difficult to navigate the spine space to implant neurostimulation leads due to scar tissue build-up. Thus, it is advantageous to perform both procedures in a single surgical setting, as disclosed herein.

Pain Management System

Figure 2:
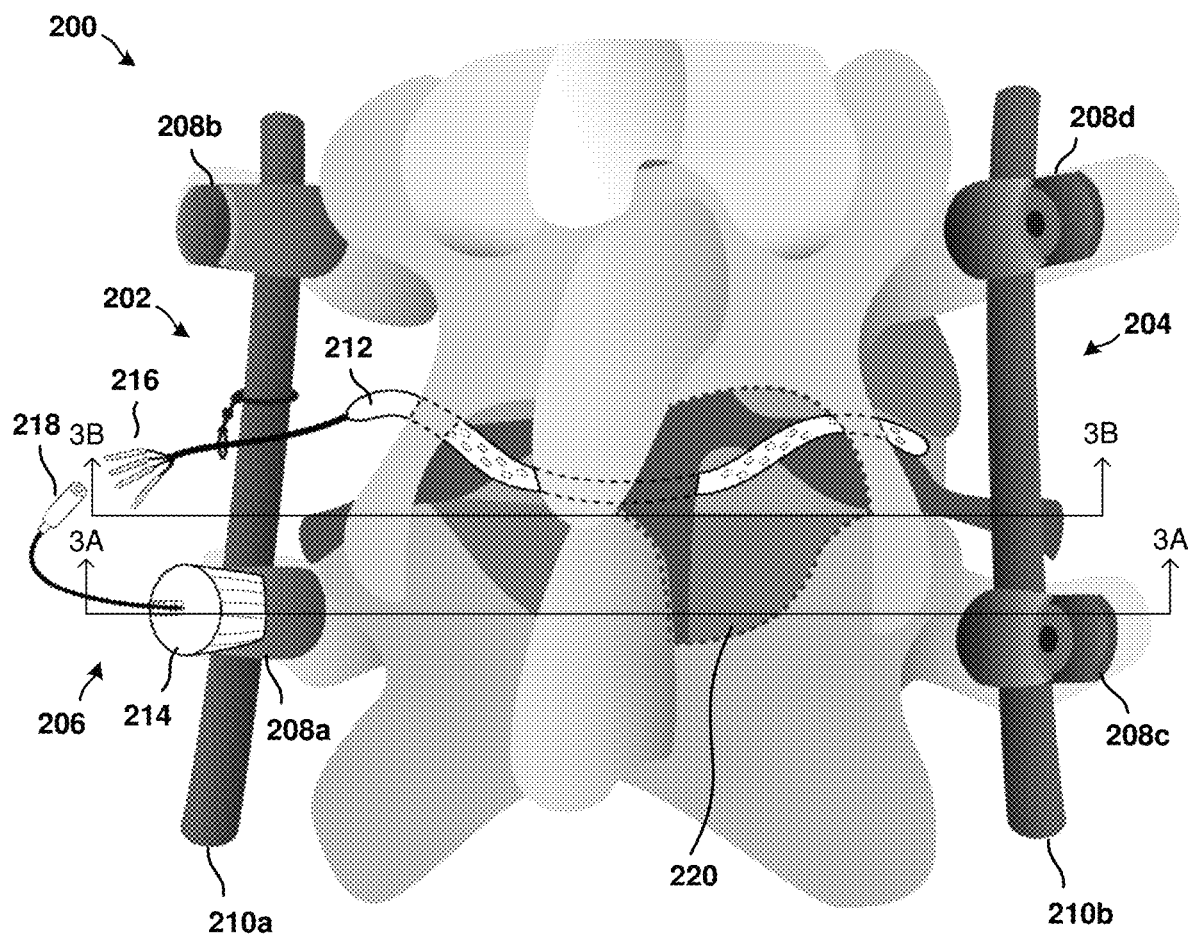
FIG. 2 is a schematic illustration of a pain management system implanted at an upper lumbar spinal level that includes a pair of spinal fixation devices including pedicle screws and rod, and a neuromodulation device that includes a ribbon lead and a therapy module configured to be mechanically coupled to and decoupled from a pedicle screw.

With reference to FIG. 2, an implantable pain management system 200 is shown implanted at an upper lumbar spinal level. The pain management system 200 includes spinal hardware in the form of a pair of spinal fixation devices 202, 204. The spinal fixation devices 202, 204 are configured to stabilize the spine as part of a spinal fusion procedure. The pain management system 200 also includes a neuromodulation device 206. The neuromodulation device 206 is configured to delivery energy to one or more nerve structures, wherein the energy results in modulation of nervous system activity. While the neuromodulation device 206 described herein deliver electrical stimulation to the target structure(s) as the main output, alternate forms of energy delivery are envisioned to modulate nerve activity, including thermal (heating or cooling), radio frequency (RF), ultrasound (mechanical, vibrations), optic (or optogenetic), laser, and magnetic.

Neuromodulation employs the body's natural biological response by stimulating nerve cell activity that can influence populations of nerves by releasing transmitters, such as dopamine, or other chemical messengers such as the peptide Substance P, that can modulate the excitability and firing patterns of neural circuits. There may also be more direct electrophysiological effects on neural membranes as the mechanism of action of electrical interaction with neural elements. The end effect is a "normalization" of a neural network function from its perturbed state. Presumed mechanisms of action for neurostimulation include depolarizing blockade, stochastic normalization of neural firing, axonal blockade, reduction of neural firing keratosis, and suppression of neural network oscillations at all levels of the central nervous system. Recent functional MRI evidence suggests that altered brain activity is associated with neuropathic pain and that neuromodulation improves this function in association with pain.

Continuing with FIG. 2, each of the spinal fixation devices 202, 204 includes a pair of pedicle screws 208a, 208b, 208c, 208d and rod 210a, 210b. These spinal fixation devices 202, 204 may be referred to herein as rod-and-screw devices. The material structure and respective dimensions of the pedicle screws 208a, 208b, 208c, 208d and rods 210a, 210b imparts a measure of stiffness, e.g., the extent to which an object resists deformation in response to an applied force, that render these components inflexible in their implanted operating environment. To this end the pedicle screws 208a, 208b, 208c, 208d may be formed of, for example, stainless steel or titanium-alloy and are dimensioned and shaped to be screwed into boney structure of the vertebrae. The rod 210a, 201b may also be formed of, for example, stainless steel or titanium-alloy and are and are dimensioned and shaped to be fixedly secured between adjacent pedicle screws implanted at different spinal levels. Upon implant of the spinal fixation devices 202, 204, the adjacent vertebrae into which the pedicle screws 208a, 208b, 208c, 208d are screwed are rendered immobile relative to each other by the rigid rod 210a, 210b spanning the screws.

The neuromodulation device 206 includes a ribbon lead 212 and a therapy module 214. The therapy module 214 is configured to mechanically couple to and subsequently decouple from a pedicle screw 208a. Likewise, the ribbon lead 212 is configured to mechanically couple to and subsequently decouple from the therapy module 210 through respective interface structures 216, 218 associated with the ribbon lead and the therapy module. When mechanically coupled to the therapy module 210, one or more electrodes at the distal end of the ribbon lead 212 are electrically coupled to circuitry within the therapy module 214.

The coupling and decoupling between respective components is such that the decoupling of one component from another does not alter or damage the structural integrity of either component. In this sense, the components may be described as being removably coupled to each other, where decoupling involves the application of minimal force. For example, the ribbon lead 212 may be decoupled from the therapy module 214 by manually pulling a connector pin of the lead interface structure 216 out of a corresponding connector port of the therapy module interface structure 218.

While the pain management system 200 shown in FIG. 2 includes only one therapy module 214 and one ribbon lead 212, additional therapy modules and ribbon leads may be included in the system. For example, in one configuration, one or more additional therapy modules may be mechanically coupled to one or more of the other pedicle screws 208b, 208c, 208d. Each additional therapy module may, in turn, be mechanically and electrically coupled to a lead. The lead to which an additional therapy module is connected may be the same ribbon lead 212 as the one that is already connected to the therapy module 214. To this end, the ribbon lead 212 may connect to the additional therapy module through one of the additional connector pins of the lead interface structure 216. Alternatively, the lead to which an additional therapy module is connected may be an additional lead (not shown). In another configuration, one or more additional ribbon leads may be mechanically and electrically coupled to a single therapy module 214. In this case, the therapy module 214 would include a therapy-module interface structure 218 with multiple connector ports, each configured to receive a respective connector pin of a ribbon lead.

Having thus generally described the components of the pain management system 200, a description of various placements of the pain management system relative to the spinal anatomy are provided below, followed by a more detailed description of the components of the neuromodulation device of the pain management system.

Placements of Pain Management System

Figure 3A:
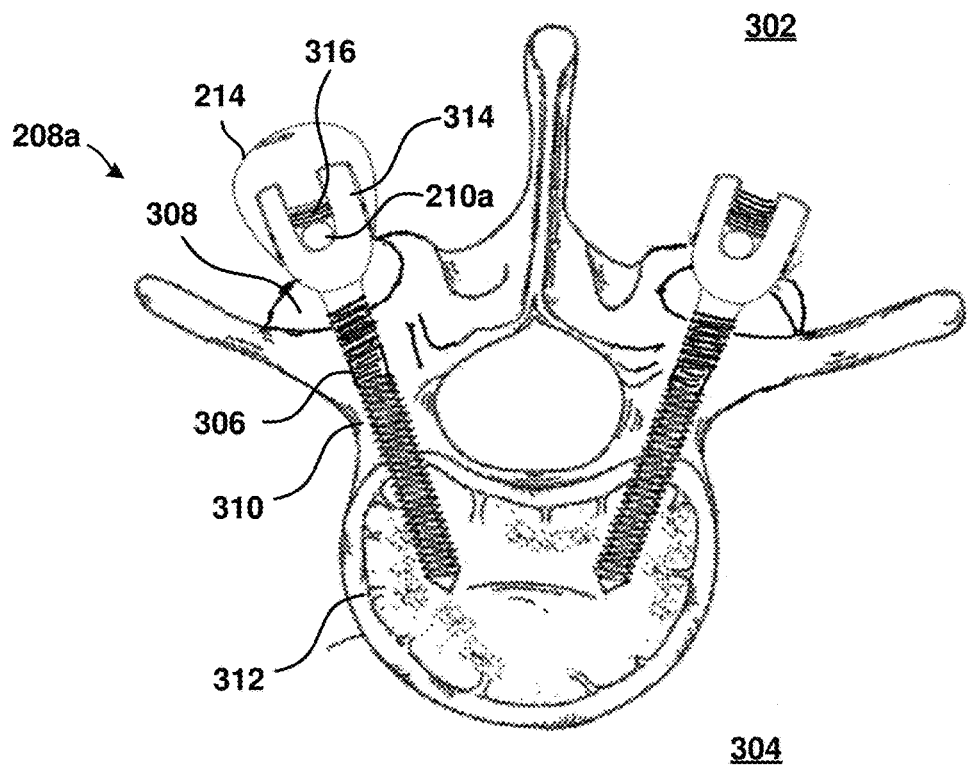
FIG. 3A is a schematic cross-section of FIG. 2 along line 3A-3A illustrating the therapy module of the neuromodulation device mechanically coupled to the pedicle screw of a spinal fixation device.

With reference to FIG. 3A, which is a cross-section of FIG. 2 along line 3A-3A, the pedicle screw 208a of the pain management system 200 of FIG. 2 is shown screwed into and extending from the posterior side 302 of the vertebrae to the anterior side 304. In doing so, a threaded portion 306 of the pedicle screw 208a passes through boney structure of the vertebrae including the vertebral arch lamina 308, the pedicle 310 and into the anterior body 312. A screw-head 314 of the pedicle screw 208a is exposed at the posterior side 302. The screw-head 314 is U-shaped and defines a cavity into which the rod 210a is placed. A threaded insert 316 engages with screw threads in the interior wall of the cavity and is rotated to engage with and secure the rod in place. The therapy module 214 of the neuromodulation device is mechanically coupled to the screw-head 314 of the pedicle screw 208a. For example, as described further below with reference to FIGS. 6A, 6B and 6C, the therapy module 214 may mechanically engage with the screw-head 314 through respective screw threads or by friction fit between respective surfaces of the therapy module and the screw-head.

Figure 3B:
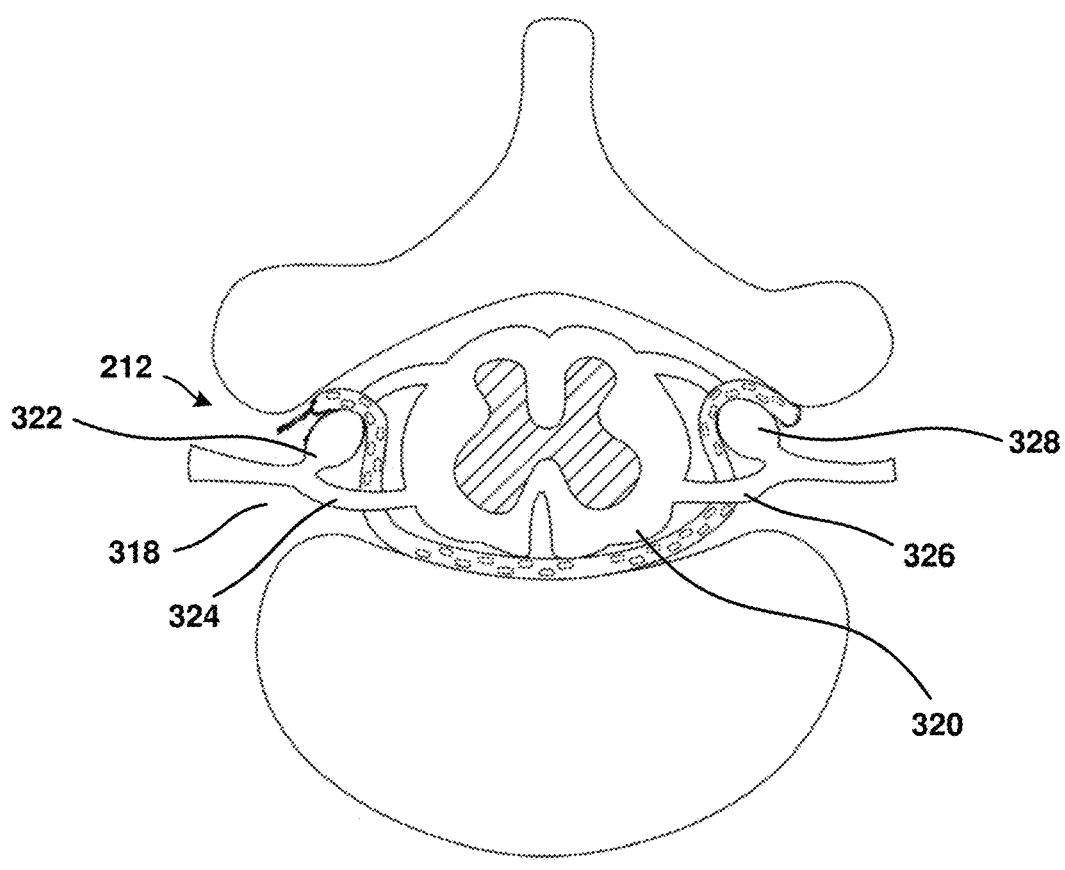
FIG. 3B is a schematic cross-section of FIG. 2 along line 3B-3B illustrating a bilateral placement of the ribbon lead of the neuromodulation device.

With reference to FIG. 3B, which is a schematic cross-section of FIG. 2 along line 3B-3B, the ribbon lead 212 of the neuromodulation device is shown placed adjacent various nerve structures in a bilateral arrangement. In this regard, bilateral refers to a lead placement that positions electrodes on or adjacent nerve structure on both sides of the spinal column midline. In the example placement shown in FIG. 3B, the electrode-bearing distal-end region of the ribbon lead 212 extends through a vertebral foramen 318 on a first side of the spinal cord 320, along a path that weaves the distal-end region through and around nerve structures such that portions of the distal-end region are positioned on or adjacent one or more of: a first dorsal root ganglion 322, a first ventral root 324, the ventral side of the spinal cord 320, a second ventral root 326, and a second dorsal root ganglion 328. Placement of the ribbon lead 212 as such enables neuromodulation of various nerves structures together with stimulation of vertebral bone or cartilage, the latter of which promotes bone growth/healing of a spinal fusion.

Figure 3C:
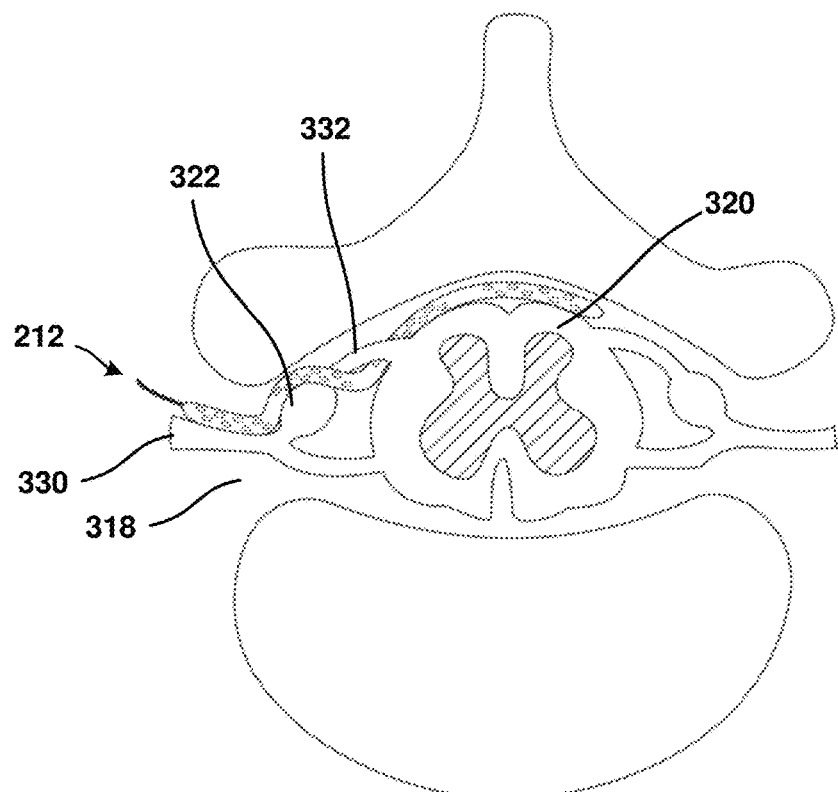
FIG. 3C is a schematic cross-section illustrating unilateral placement of a ribbon lead an upper lumbar spinal level.

With reference to FIG. 3C, the ribbon lead 212 of the neuromodulation device is shown placed adjacent various nerve structures in a unilateral arrangement. In this regard, unilateral refers to a lead placement that positions electrodes on or adjacent nerve structure on one side of the spinal column midline. In the example placement shown in FIG. 3C, the electrode-bearing distal-end region of the lead extends through a vertebral foramen 318 on a first side of the spinal cord 320, along a path that weaves the distal-end region through and around nerve structures such that portions of the distal-end region are positioned on or adjacent one or more of: a first spinal nerve 330, a first dorsal root ganglion 322, a first dorsal root 332, and a portion of the dorsal side of the spinal cord 320. Placement of the ribbon lead 212 as such enables neuromodulation of various nerves structures together with stimulation of vertebral bone or cartilage, the latter of which promotes bone growth/healing of a spinal fusion.

With reference to FIG. 2, placement of the lead as shown in FIGS. 3B and 3C may occur during implant of the spinal fixation devices 202, 204. To this end, during spinal fusion a laminectomy and/or laminotomy may be performed to gain access to a spinal disc. As a result, a surgical opening 220 is available through which a surgeon has direct access to the nerve structures. Accordingly, the distal-end region of the ribbon lead 212 may be placed and weaved through and around the nerve structures without the need for traditional lead delivery tools. For example, in the open access procedure afforded by the surgical opening 220, the surgeon does not have to access the spinal column region using a percutaneous sheath or catheter, nor does the surgeon have to advance the lead through such delivery tools.

Figure 3D:
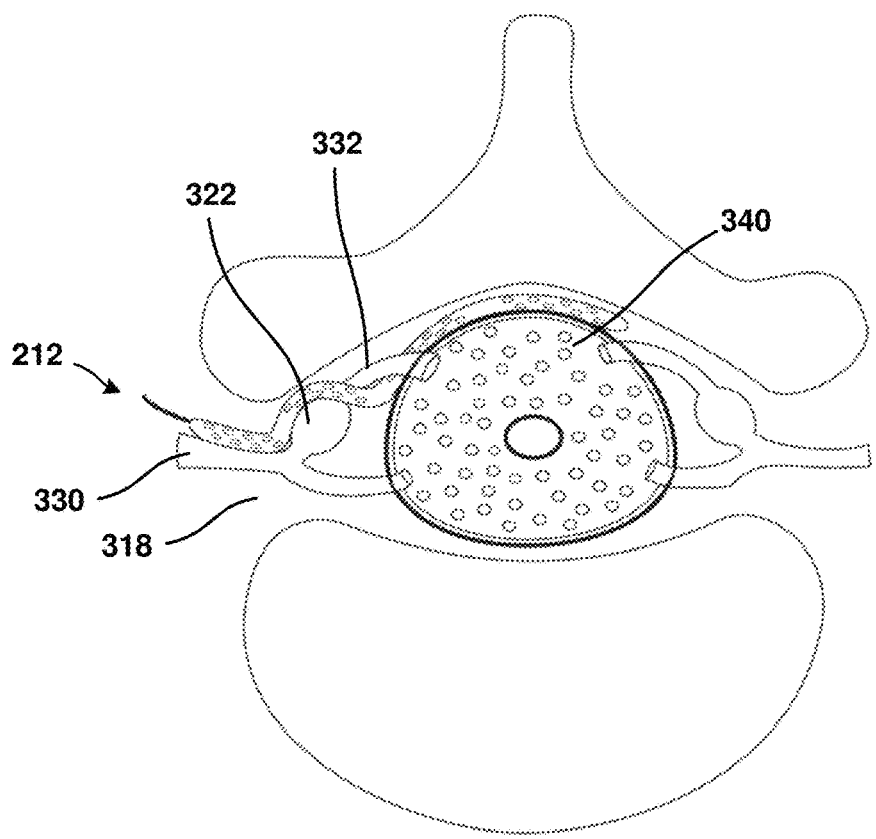
FIG. 3D is a schematic cross-section illustrating unilateral placement of a ribbon lead at a lower lumbar spinal level.

With reference to FIG. 3D, which is a schematic cross-section of a ribbon lead 212 implanted at a lower lumbar spinal, the ribbon lead 212 of the neuromodulation device is placed adjacent various nerve structures in a unilateral arrangement. In the example placement shown in FIG. 3D, the electrode-bearing distal-end region of the lead extends through a vertebral foramen 318 on a first side of the spinal cord 320, along a path that weaves the distal-end region through and around nerve structures such that portions of the distal-end region are positioned on or adjacent one or more of: a first spinal nerve 330, a first dorsal root ganglion 322, a first dorsal root 332, and a portion of the dorsal side of the Conus Medularis/Cauda equina 340. Placement of the ribbon lead 212 as such enables neuromodulation of various nerves structures together with stimulation of vertebral bone or cartilage, the latter of which promotes bone growth/healing of a spinal fusion.

Neuromodulation Device

Figure 4:
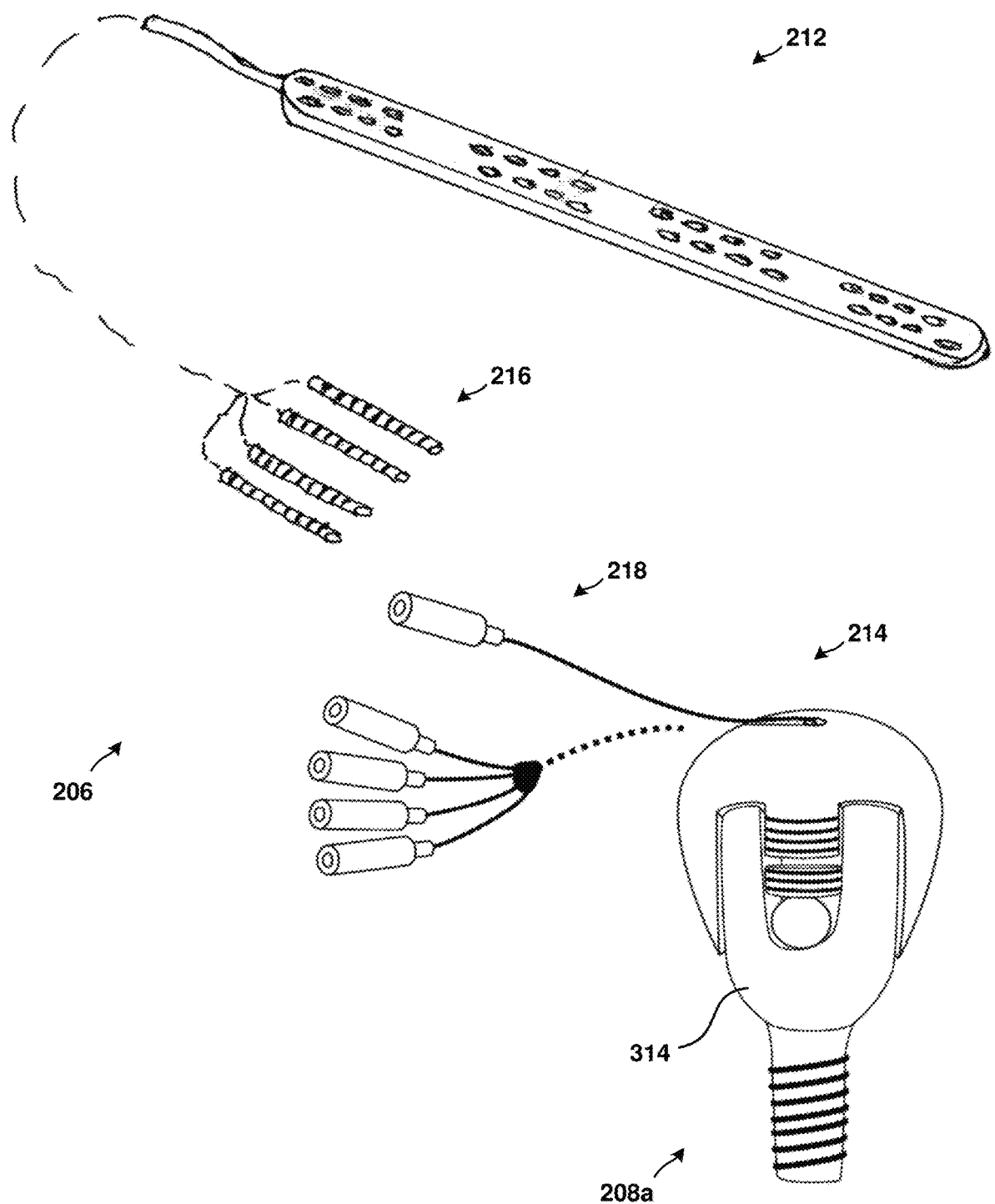
FIG. 4 is an illustration of components of the pain management system of FIG. 2 including a pedicle screw, a therapy module coupled to the screw-head of the pedicle screw, and a ribbon lead.

With reference to FIG. 4, as disclosed above, the neuromodulation device 206 disclosed herein includes a ribbon lead 212 and a therapy module 214. The therapy module 214 is configured to mechanically coupled to and decoupled from the screw-head 314 of a pedicle screw 208a. Likewise, the ribbon lead 212 is configured to mechanically couple to and subsequently decouple from the therapy module 214 through respective interface structures 216, 218 associated with the ribbon lead and the therapy module. When mechanically coupled to the therapy module 210, one or more electrodes at the distal end of the ribbon lead 212 are electrically coupled to circuitry within the therapy module 214.

Ribbon Lead

With reference to FIGS. 5A-5D, the ribbon lead 212 includes a distal-end region 502 and proximal-end region 504. The distal-end region 502 includes a flexible, thin ribbon structure 506 having a plurality of first electrodes 508 arranged within its first side 510 and a plurality of second electrodes 512 arranged within its second side 514. The flexible, thin ribbon structure 506 may be made of a flexible biocompatible polymer (e.g., silicone) having a Shore hardness selected provide the ribbon structure a high degree of flexibility, to make the ribbon structure soft, floppy, and ductile. To this end, the Shore hardness may be on the order of 60A. The ribbon structure 506 may have a thickness in the range of 0.25 mm to 1 mm. The respective electrodes 508, 512 on each side are electrically isolated from each other by insulative material of the ribbon structure 506. Furthermore, the ribbon structure 506 may include a layer of insulative material that is sandwiched between the first electrodes 508 on the first side 510 and the second electrodes 512 on the second side 514 to prevent electrical interference between electrodes on opposite sides.

In the example ribbon lead 212 shown in FIGS. 5A-5D, the ribbon structure 506 includes two rows of electrodes 508 on its first side 510 and two rows of electrodes 512 on its second side 514, with each row having sixteen electrodes. Thus, each side of the ribbon structure 506 has thirty-two electrodes 508, 512 arranged in a pattern corresponding to a 2-by-16, two-dimensional array. Of course, different numbers of electrodes may be included in the ribbon structure 506 and different two-dimensional array patterns may be formed by the electrodes. For example, in other embodiments of the ribbon lead 212, the ribbon structure 506 may include sixteen electrodes on each side arranged in a 2-by-8 two-dimensional array for a total of thirty-two electrodes, or twenty-four electrodes on each side arranged in a 2-by-24 two-dimensional array for a total of forty-eight electrodes.

The electrodes 508, 512 are preferably formed of a non-corrosive, highly conductive material. Examples of such material include stainless steel, MP35N, platinum, and platinum alloys. The electrodes 508, 512 may be separately formed and integrated into the silicone material of the ribbon structure 506. In this case, the electrodes 508, 512 may have a thickness in the range of 0.05-0.2 mm. Alternately, the ribbon structure 506 may be manufactured using thin film technology, in which case the electrodes 508, 512 may formed on respective sides of a substrate layer forming part of the ribbon structure, using thin film deposition. In this case, the electrodes 508, 512 may have a thickness in the range of 0.01-0.1 mm. In either case, the surfaces the electrodes 508, 512 are substantially flush with the surfaces of the ribbon structure 506. In another example, the ribbon structure 506 could be a custom printed lead based on individual patient anatomy (e.g., selective nerve root anatomy). The anatomy could be obtained by scanning the patient's nerve/spine area to get the dimensions and then taking the contour and dimension input to custom print the lead.

One or more sensors may be associated with the ribbon structure 506. For example, the ribbon structure 506 may have a plurality of first temperature sensors 509 arranged within its first side 510 and a plurality of second temperature sensors 513 arranged within its second side 514, for providing temperature feedback signals to the therapy module 214. Each temperature sensor may be associated with a group or cluster of electrodes 508, 512.

The ribbon structure 506 is configured to have utmost flexibility to enable placement of electrodes at one or more nerve structures during an open surgical procedure. In addition to the above described material composition and thickness of the ribbon structure 506, additional features of the ribbon structure impart the desired flexibility. These additional features include: 1) the arrangement of the electrodes 508, 512 relative to each other on the same side of the ribbon structure, 2) the arrangement of the electrodes 508, 512 relative to each other on the opposite sides of the ribbon structure, and 3) the size of the electrodes and the interelectrode spacing.

Same-Sided Electrode Arrangement

Figure 5A:
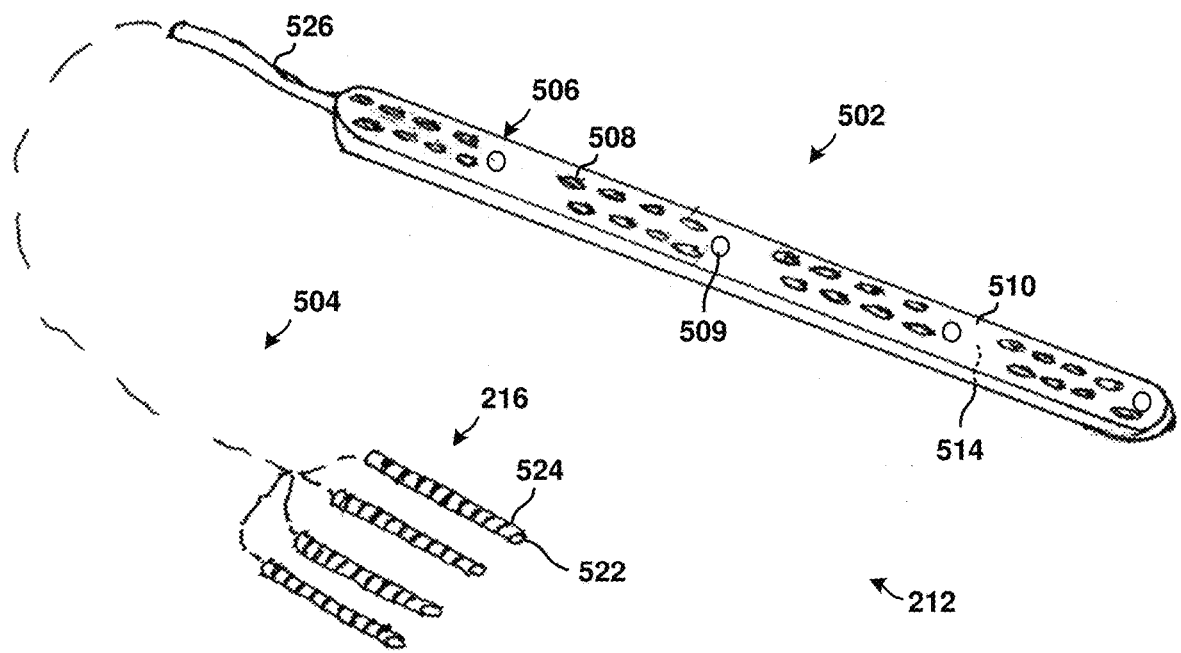
FIG. 5A is an illustration of the ribbon lead of FIG. 4 including an electrode-bearing ribbon structure having electrodes on both sides.
Figure 5B:
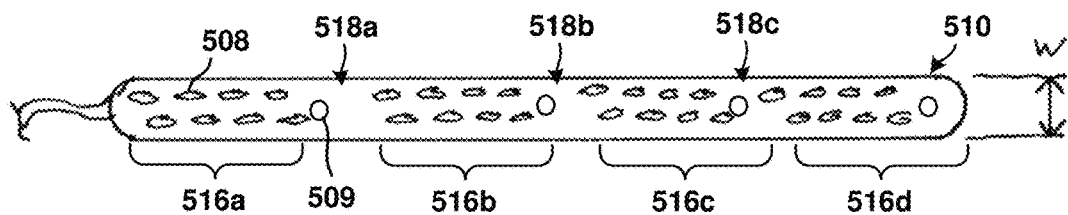
FIGS. 5B, 5C and 5D are top, bottom and side views of the ribbon lead of FIG. 5A.
Figure 5C:
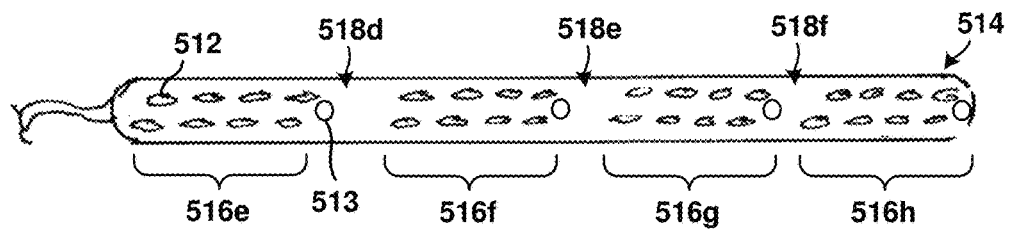
Figure 5D:
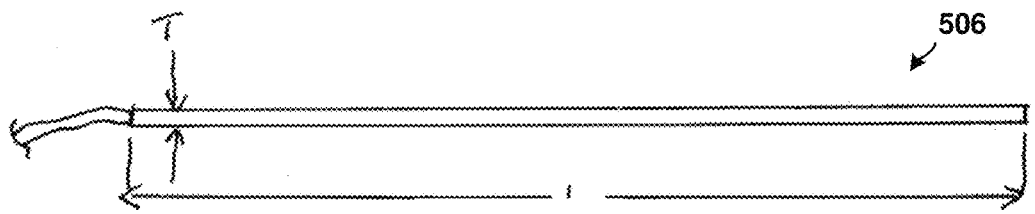

With reference to FIGS. 5B and 5C, the electrodes 508, 512 on each side 510, 514 are arranged in a pattern selected to improve flexibility of the ribbon structure 506. To this end, while the electrodes 508, 512 are substantially aligned along the length of the ribbon structure 506, they are offset or staggered relative to each other across the width of the ribbon structure. Thus, the ribbon structure 506 is devoid of rigid regions that would otherwise result if two electrodes 508, 512 on the same side were aligned side-by-side across the width. This staggering of same-sided electrodes improves the flexibility of the ribbon structure 506 both along it length and across its width. In another configuration, the electrodes 508, 512 are substantially aligned along the length of the ribbon structure 506 and across the width of the ribbon structure. Thus, the ribbon structure 506 has alternates along its length between regions that are devoid of any electrodes and thus highly flexible, and regions having side-by-side electrodes across its width that are less flexible.

Opposite-Sided Electrode Arrangement

With reference to FIG. 5E, the arrangement of respective electrodes 508, 512 on respective sides 510, 514 of the distal-end region 502 of the ribbon lead 212 may be such that the electrodes on opposite sides are staggered or offset relative to each other. In other words, the first pattern of first electrodes 508 and the second pattern of second electrodes 512 arrange the plurality of first electrodes and the plurality of second electrodes relative to each other so that no first electrode aligns with a second electrode along an axis 515 extending perpendicular through an electrode and through the ribbon structure 506.

In an alternate configuration, shown in FIG. 5F, the arrangement of respective electrodes 508, 512 on respective sides 510, 514 of the distal-end region 502 of the ribbon lead 212 may be such that the electrodes on opposite sides are stacked or aligned relative to each other. In other words, the first pattern of first electrodes 508 and the second pattern second electrodes 512 arrange the plurality of first electrodes and the plurality of second electrodes relative to each other so that a first electrode aligns with a second electrode along an axis 517 extending perpendicular through and electrode and through the ribbon structure.

Each of these arrangements has its advantages. For example, the staggered arrangement shown in FIG. 5E provides greater spacing between opposite-sided electrodes, thus reducing current leakage between the electrodes. The staggered arrangement may also provide for easier manufacturing using thin film plating technology. The stacked arrangement shown in FIG. 5F provides ribbon structure 506 with regions that are devoid of metal electrodes on each of its side, thus allowing for more flexibility of the distal-end region.

While the foregoing describes alternate configurations where the opposite-sided electrodes are either aligned or offset, other arrangement are possible. For example, opposite-sided electrodes may be partially aligned such that only portions of the electrodes overlap. In an example of one such configuration, opposite-sided electrodes may be arranged so that there is a 50% overlap between the respective surfaces of the electrodes.

Electrode Size and Spacing

In the ribbon lead 212 illustrated in FIG. 5A-5E, the electrodes 508, 512 are long and narrow in the shape of a hockey ring. In this configuration, the electrodes 508, 512 may have a length in the range of 2 mm to 4 mm and a width in the range of 0.25 mm and 2 mm. The spacing between adjacent electrodes along the length of the ribbon structure 506 is no more than two times the length of the electrodes. The spacing between adjacent electrodes across the width of the ribbon structure 506 is no more than two times the width of the electrodes. The ribbon lead 212, however, does not require electrodes in the shape and size just described. The electrodes 508, 512 may have different shapes, including for example square, oval, circular, etc.

The electrode size and interelectrode spacing according to representative embodiments provide sufficient resolution to control the stimulation of target nerve structure, such as those described above with reference to FIGS. 3B and 3C. Additionally, the electrode clusters 516a-d, 516e-h provide a degree of positional tolerance during the surgical placement of distal-end region 502 of the ribbon lead 212 in the area of the spinal column, because it is likely that at least one of the electrode clusters can be appropriately placed to stimulate a target nerve structure. Also, if the distal-end region 502 is displaced relative to a target nerve structure subsequent to implantation due to migration or flipping of the ribbon structure 506, the stimulation applied to that target nerve structure can be shifted to different electrodes 508, 512 on the same side of the ribbon structure (in the case of longitudinal movement of the ribbon structure) or to electrodes on the opposite side of the ribbon structure (in the case of flipping or twisting of the ribbon).

With reference to FIGS. 5A-5D, in one embodiment the thirty-two electrodes 508, 512 on each side are grouped into four electrodes clusters, each having eight electrodes. Thus, the ribbon lead 212 has a total of eight electrode clusters, with four clusters 516a-d on the first side and four clusters 516e-h on the second side. In one configuration, adjacent electrode clusters 516a-d, 516e-h on each side are separated from each other by an area of insulative material 518a-c, 518d-f. The areas of insulative material 518a-c, 518d-f between adjacent electrode clusters 516a-d, 516e-h provide the distal-end region 502 of the ribbon lead 212 with regions of higher flexibility. Specifically, the metal structure of the electrodes 508, 512 makes those areas of the distal-end region 502 corresponding to the electrode clusters 516a-d, 516e-h somewhat less flexible than the electrode-free areas of the distal-end region 502 corresponding to the area of insulative material 518a-c, 518d-f.

While the embodiment of the ribbon structure 506 depicted in FIGS. 5A-5D includes electrode clusters 516a-d, 516e-h that are spaced apart, such spacing is optional. Accordingly, in other embodiments, the electrodes 508, 512 are evenly spaced along the length of the ribbon structure 506. The electrodes 508, 512 may still be grouped into clusters, however, such groupings are functional in nature—not physical. Thus, as used herein the term "cluster" does not confer any sort of spacing requirement between groups of electrodes.

Placement of the Lead

With continued reference to FIG. 5A-5D, the distal-end region 502 may have one of several lengths (L) depending on the intended placement application of the ribbon lead 212. For example, in one embodiment, a ribbon lead 212 for placement in a bilateral arrangement as described above with reference to FIG. 3B may have a length (L) in the range of 5 cm to 8 cm. In another embodiment, a ribbon lead 212 for placement in a unilateral arrangement as described above with reference to FIG. 3C may have a length (L) in the range of 2 cm to 5 cm. The width (W) of the distal-end region 502 in the range of 2 mm to 5 mm and is sized to accommodate two rows of electrodes. The thickness (T) of the distal-end region 502 in the range of 0.25 mm to 1 mm. Depending on the length, one or more electrode features of the ribbon structure 506 may be modified. For example, a shorter length ribbon structure 506 may have fewer electrodes than a longer length ribbon structure. Alternatively, the number of electrodes may be the same, but the size of the electrodes in the shorter ribbon structure may be smaller than the electrodes in the longer length ribbon. In yet another alternative, the number and size of electrodes may be the same, but the interelectrode spacing in the shorter ribbon structure may be less than in the longer ribbon structure.

In some embodiments, a ribbon lead 212 can be implanted within a patient such that the distal-end region 502 and its associated electrodes 508, 512 are positioned at a spinal level at or near one or more nerve structures associated with that spinal level. For example, as previously described with reference to FIG. 3B, the distal-end region 502 of the ribbon lead may be weaved through a spinal level such that electrodes 508, 512 are located near the DRG on each side of the spinal cord at that level and electrodes are located at the spinal cord.

After implantation, an electrode combination at one or more electrode clusters may be determined that is effective for treating pain. For example, with reference to FIG. 3B, an electrode combination in the electrode cluster near the first dorsal root ganglion 322 may be selected to deliver stimulation energy to first dorsal root ganglion. Another electrode combination in the electrode cluster near the a first ventral root 324 may be selected to deliver stimulation energy to a first ventral root. Yet another electrode combination in the electrode cluster near the anterior side of the spinal cord 320 may be selected to deliver stimulation energy to spinal cord. After the determination of the appropriate electrodes for stimulation, the therapy module can be programmed to deliver pulses using the first and second rows according to the determined electrode combinations.

Interconnection of the Lead

With reference to FIG. 5A, the ribbon lead 212 includes a lead interface structure 216 for mechanically and electrically connecting the lead to a therapy module 214. A tubular lead body 526 extends between the ribbon structure 506 and the lead interface structure 216. Conductors embedded within the flexible, thin ribbon structure 506 extend through the lead body 526 to enable electrical connection between electrodes 508, 512 and contacts associated with the interface structure 520.

In one embodiment, the lead interface structure 216 comprises four in-line connector pins 522, each having nine electrical contacts 524. Each connector pin 522 is switchably connected to a one of the eight electrode clusters 516a-d, 516e-h. The switchable connection may be provided by multiplexer circuitry included in the lead. The multiplexer circuitry could be controlled using a logic circuit in the ribbon lead 212 that is configured to receive control signals from the therapy module. The logic circuit responds to the signals by setting the multiplexer circuitry as appropriate. Upon connection between a connector pin 522 and an electrode cluster, eight of the nine electrical contacts 524 connect to a respective electrode 508, 512 in the connected electrode cluster 516a-d, 516e-h. The remaining ninth electrical contact 524 of the connector pin 522 functions as a ground or an inactive set screw site.

Lead Functionality

Thus disclosed is a ribbon lead 212 having a two-dimensional array of electrodes along a length of its distal-end region, configured to have utmost flexibility to enable placement of electrodes at one or more nerve structures during an open surgical procedure. Because the lead is placed during an open procedure and is intended to weave around and between nerve structures, while also providing electrodes arrangements that enable the targeting of multiple nerve structures and electrode shifting, design features associated with traditional percutaneous leads or paddle leads are avoided. For example, a paddle lead place in the epidural space is designed so that the paddle region of the lead assumes a substantially planar shape. While the paddle region of such leads may be forcibly bent, the paddle region is configured such that upon removal of such force the paddle region bounces back to its substantially planar shape.

In the ribbon lead 212 disclosed herein, the ribbon structure 506 is configured, via one or more of ribbon structure thickness, electrode shape and size, interelectrode spacing, same-sided electrode arrangements, opposite-side electrode arrangements, to assume non-planar configurations upon the application of a force. Such forces may include, for example, bending or twisting forces that a surgeon may apply to the lead during open procedure placement. The flexibility of the ribbon structure 506, however, is such that the ribbon structure retains the non-planar configuration upon removal of the force. In other words, the ribbon structure is floppy and flexible so that once it is placed by a surgeon via bending, twisting, weaving, etc., the ribbon structure conforms to the anatomy and remains conformed after the surgeon finally places the lead and is no longer applying any type of force to it.

With reference to FIG. 5G, the ribbon structure 506 is configured to assume and retain an undulated configuration along its longitudinal axis. In other words, the ribbon structure 506 is configured to bend in response to the application of a bending force, in at least one curve, or a series of successive curves in alternating directions along a longitudinal axis 519 extending down the center of the ribbon structure. In the example state shown in FIG. 5G, the ribbon structure 506 assumes sharper curves in the electrode-free regions. i.e., areas of insulative material 518a-c, 518d-f, relative to slight curves assumed in the electrode cluster 516a-d, 516e-h regions.

With reference to FIG. 5H, the ribbon structure 506 is also configured to assume and retain an undulated configuration in regions of insulative material 530 between adjacent electrodes 508, 512. In the example shown in FIG. 5H, the ribbon structure 506 is configured so that the electrodes 508, 512 are evenly distributed along the length of the ribbon structure. Thus, unlike the example shown in FIG. 5G, there are no large areas of insulative material 518a-c, 518d-f between adjacent electrode clusters 516a-d, 516e-h, and the ribbon structure 506 assumes tighter curves, e.g. lower radius of curvature, than the curves of FIG. 5G. In one configuration, the ribbon structure 506 assumes curves having a radius of curvature 531 in the range of 1 mm and 3 mm. Note that, while it is possible for a ribbon structure to curve at every spacing between adjacent electrodes, for ease of illustration, the ribbon structure 506 shown in FIG. 5H curves at every other occurrence of a spacing between adjacent electrodes.

With reference to FIG. 5I, the ribbon structure 506 is configured to assume and retain a twisted configuration about its longitudinal axis. In other words, the ribbon structure 506 is also configured such that opposed edges 521a, 521b of the ribbon structure curve in response to the application of a twisting force, about a longitudinal axis 523 extending down the center of the ribbon structure.

Regarding traditional percutaneous leads, while these leads may be more flexible than known paddle leads, percutaneous leads by design have a linear array of ring electrodes and possibly a tip electrode. These leads do not have a two-dimensional array of electrodes that enable high resolution targeting of multiple nerve structures by electrode shifting Therapy Module With reference to FIGS. 6A, 6B, 6C, and 6D, the therapy module 214 of an implantable neuromodulation device 206 includes a housing 602 that encloses various electronic components. The housing 602 may be formed of biocompatible metal, such as titanium and has a form factor that includes one or more features configured to mate with a corresponding feature of a screw-head 314 of a pedicle screw 208a. In some configuration, one or more portions of the housing may be formed of or coated with a layer of a pliable, biocompatible material, such as a low durometer rubber or rubber-like material, e.g., silicone. Alternatively, the housing may be formed of a combination of biocompatible, non-metal materials including for example, a majority of housing may be formed of a polymer thermoplastic such as poly-ether-ether-ketone (PEEK), with certain features being coated with or formed of pliable silicone. The respective features mate in a manner that enables the therapy module 214 to mechanically couple to and subsequently decouple from the screw-head 314. The coupling and decoupling between the therapy module 214 and the screw-head 314 is such that the decoupling of one component from another does not alter or damage the structural integrity of either component. In this sense, the components may be described as being removably coupled to each other, where decoupling involves the application of minimal force.

Figure 6A:
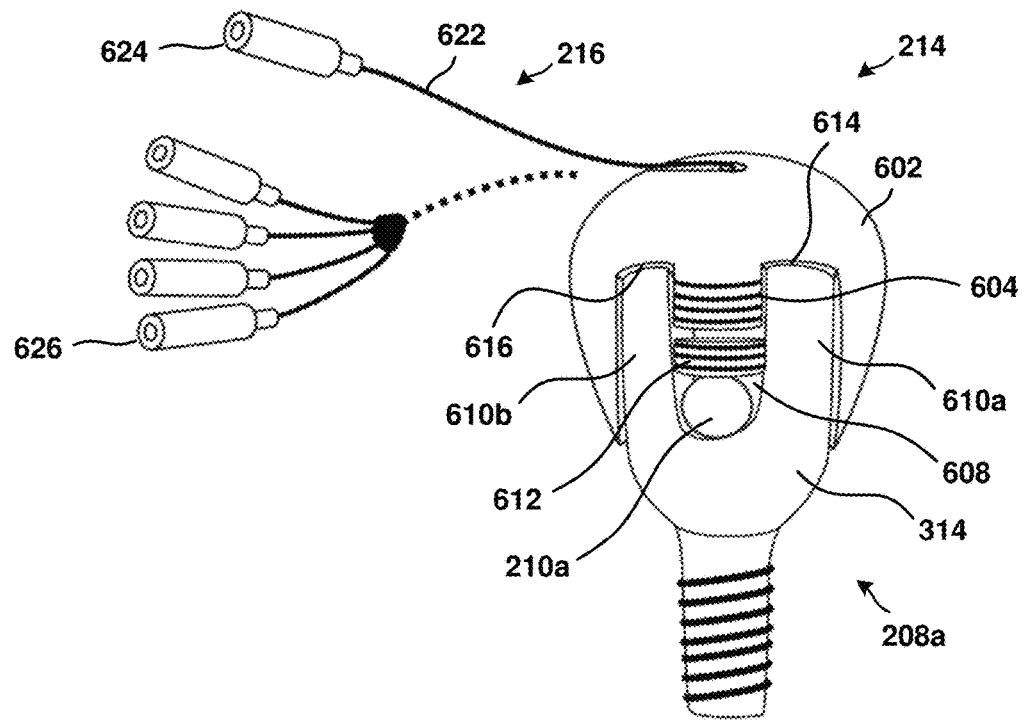
FIG. 6A is a schematic illustration of the therapy module of FIG. 4 coupled to the screw-head of the pedicle screw.
Figure 6B:
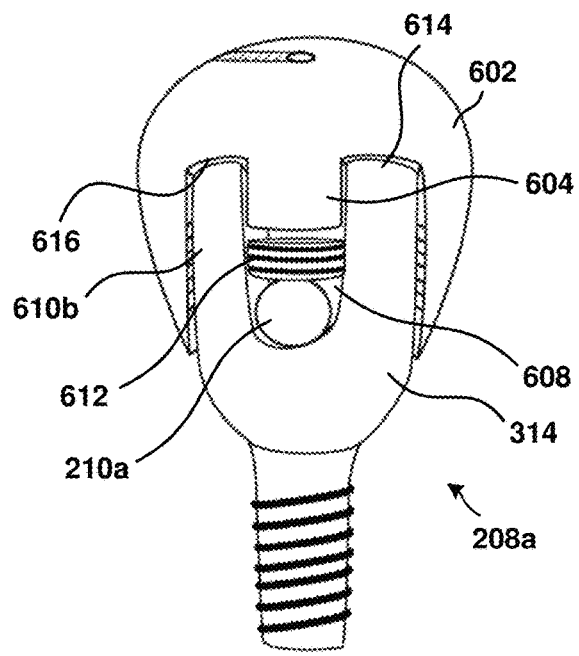
FIGS. 6B and 6C are alternate embodiments of the therapy module of FIG. 6A.

With reference to FIGS. 6A and 6B, the mating feature of the housing 602 may be a center projection 604 having an outer wall 606, and the corresponding mating feature of the screw-head 314 is a screw-head cavity 608. The screw-head cavity 608 is defined by the space between opposed sides 610 of the screw-head 314. The lower portion of the screw-head cavity 608 is configured to receive a rod 210a of a rod-and-screw stabilization device and a threaded insert 612. The threaded insert 612 engages threads formed in the inner walls of the opposed sides 610 of the screw-head 314 and advances downward toward the rod 201a during rotation to engage a portion of the rod and secure it in place.

In the therapy module 214 configuration shown in FIG. 6A, the outer wall 606 of the center projection 604 is threaded and like the thread insert 612, it too engages the threads formed in the inner walls of the opposed sides 610 of the screw-head 314 and advances downward toward the threaded insert 612 during rotation until the top surface 614 of the screw-head 314 is in abutting contact with an under surface 616 of the housing 602. Thus, in this configuration the therapy module 214 is coupled to the screw-head 314 by threaded rotation and may be subsequently decoupled by threaded rotation without altering or damaging the structural integrity of either the therapy module 214 or the screw-head 314.

In the therapy module 214 configuration shown in FIG. 6B, the center projection 604 of the housing 602 is sized such that the center projection tightly fits into the screw-head cavity 608. As such, the outer wall 606 of the projection engages the inner walls of the opposed sides 610 of the screw-head 314 to establish a tight friction fit that secures the housing 602 to the screw-head 314. To facilitate this friction fit, the center projection may be formed of or coated with a pliable material, e.g., a plastic, that compress upon force to tightly fits into the screw-head cavity 608. The housing 602 may be pushed downward toward the threaded insert 612 until the top surface 614 of the screw-head 314 is in abutting contact with an under surface 616 of the housing 602. Thus, in this configuration the therapy module 214 is coupled to the screw-head 314 by a push force and may be subsequently decoupled by a pull force without altering or damaging the structural integrity of either the therapy module 214 or the screw-head 314.

Figure 6C:
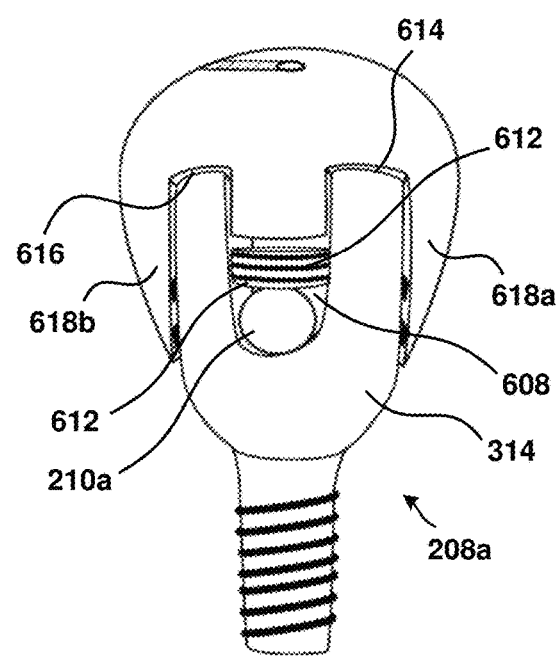

With reference to FIG. 6C, the mating feature of the housing 602 may be a pair of opposed side projections 618a, 618b that define a housing cavity 620, and the corresponding mating feature of the screw-head 314 is a portion of the screw-head itself. The housing cavity 620 is defined by the space between opposed side projections 618a, 618b of the housing 602, and is configured to receive the portion of the screw-head 314. In this configuration, the screw-head 314 also has a screw-head cavity 608 configured to receive a rod 210a of a rod-and-screw stabilization device and a threaded insert 612 to engage a portion of the rod and secure it in place.

In one configuration, the inner walls of the opposed side projections 618a, 618b are threaded and engage with corresponding threads formed in the outer wall of the screw-head 314. Thus, in this configuration the therapy module 214 is coupled to the screw-head 314 by threaded rotation and may be subsequently decoupled by threaded rotation without altering or damaging the structural integrity of either the therapy module 214 or the screw-head 314.

In another configuration, the housing cavity 620 of the housing 602 is sized such it tightly fits over the screw-head 314. As such, the inner walls of the opposed side projections 618a, 618b engage the outer wall of the screw-head 314 to establish a tight friction fit that secures the housing 602 to the screw-head 314. To facilitate this friction fit, the inner walls of the opposed side projections 618a, 618b may be coated with a pliable material, e.g., a plastic, that compresses upon force to tightly fit over the screw-head 314. The housing 602 may be pushed downward over the screw-head 314 until the top surface 614 of the screw-head 314 is in abutting contact with an under surface 616 of the housing 602. Thus, in this configuration the therapy module 214 is coupled to the screw-head 314 by a push force and may be subsequently decoupled by a pull force without altering or damaging the structural integrity of either the therapy module 214 or the screw-head 314.

Continuing with FIG. 6A, the therapy module 214 includes a therapy-module interface structure 218 configured to couple with a lead interface structure. In one configuration, the therapy-module interface structure 218 is a dongle 622 having an in-line connector structure 624 configured to mate with a corresponding connector structure of the lead interface structure. In another configuration, the dongle 622 has four in-line connector structures 626.

Figure 6D:
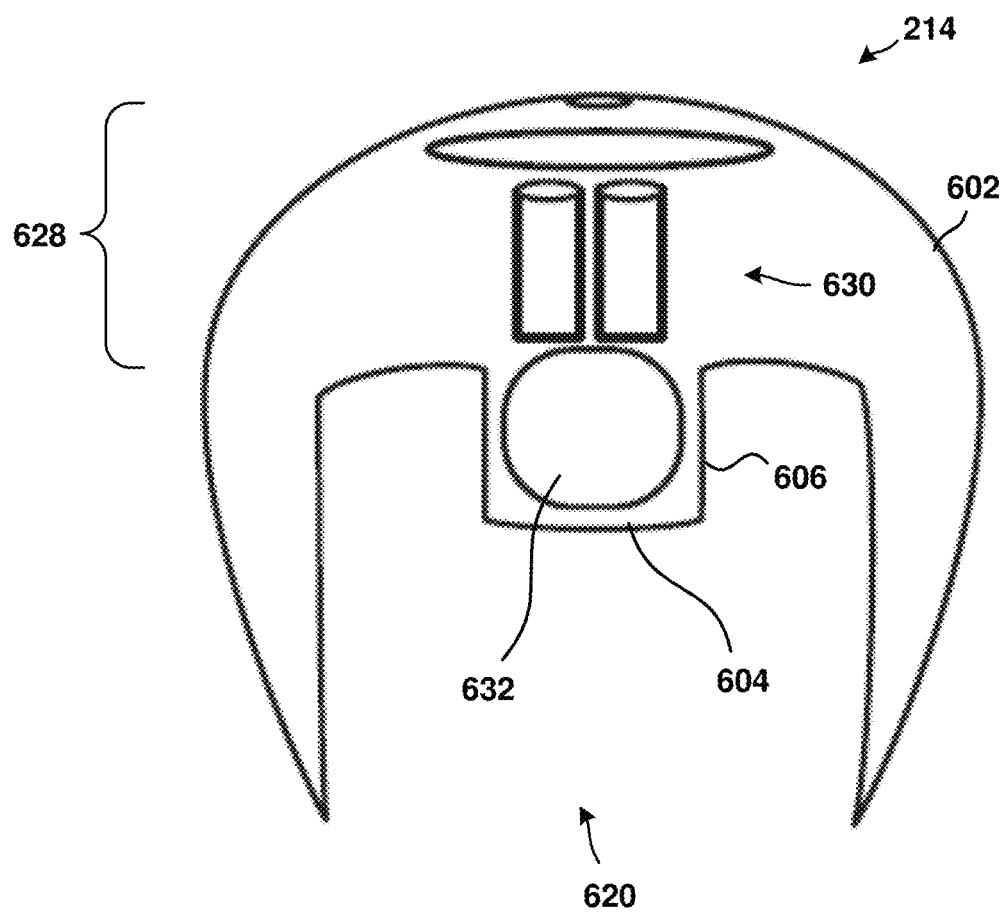
FIG. 6D is a schematic illustration of the electronic components of anyone of the therapy modules of FIGS. 6A, 6B and 6C.

With reference to FIG. 6D, the electronic components 630 of the therapy module 214 are mostly located in a upper region 628 of the housing 602. Some electronic components, however, may be located in other portions of the housing. For example, the energy source 632, e.g., battery or inductively charged capacitors, may be located inside of the projection 604. The battery may be a wireless rechargeable or non-rechargeable (i.e., primary cell). The battery may be an ultra thin film battery, or single layer carbon fiber battery. The battery could be in the shape of a button cap. Further description of the electronic components 630 of the therapy module 214 are provided below with reference to FIGS. 9-12.

Figure 7:
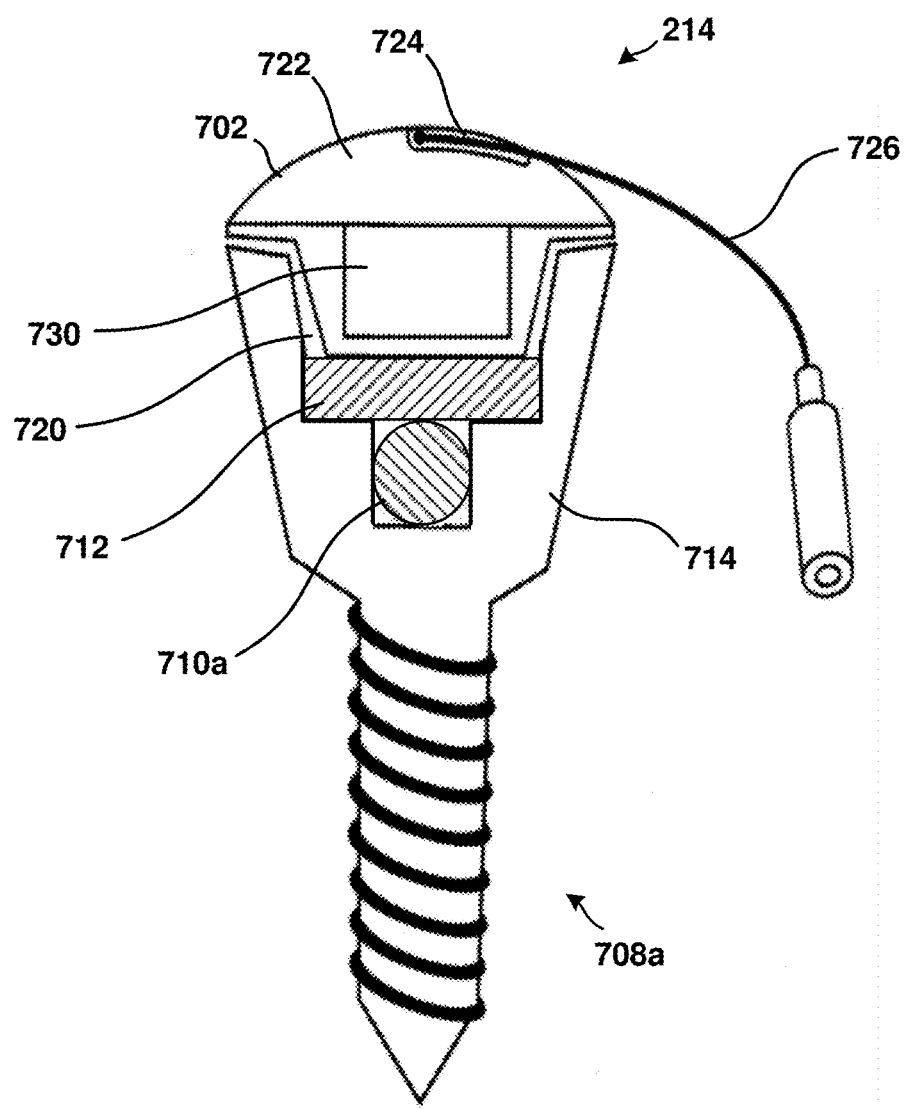
FIG. 7 is a schematic illustrations of alternate embodiments of a therapy module coupled to the screw-head of the pedicle screw.

With reference to FIG. 7, in an alternate embodiment of a therapy module 214 configured for use with a pedicle screw 708a having a larger screw-head cavity 720, most of the electronic components 730 are located in a portion of the housing 702 that lies within the screw-head cavity 720 just above the threaded insert 712. The therapy module 214 may be coupled and decoupled from the screw-head 714 in anyone of the ways described above with reference to FIGS. 6A, 6B and 6C. The form factor of the housing 702 includes a domed top 722 that projects above the top of the screw-head 714. The domed top 722 may be formed of or coated with a layer of pliable material that includes a groove 724. The groove 724 is configured to receive and secure in place, a portion of a dongle wire 726 that extends from the housing 702.

Figure 8:
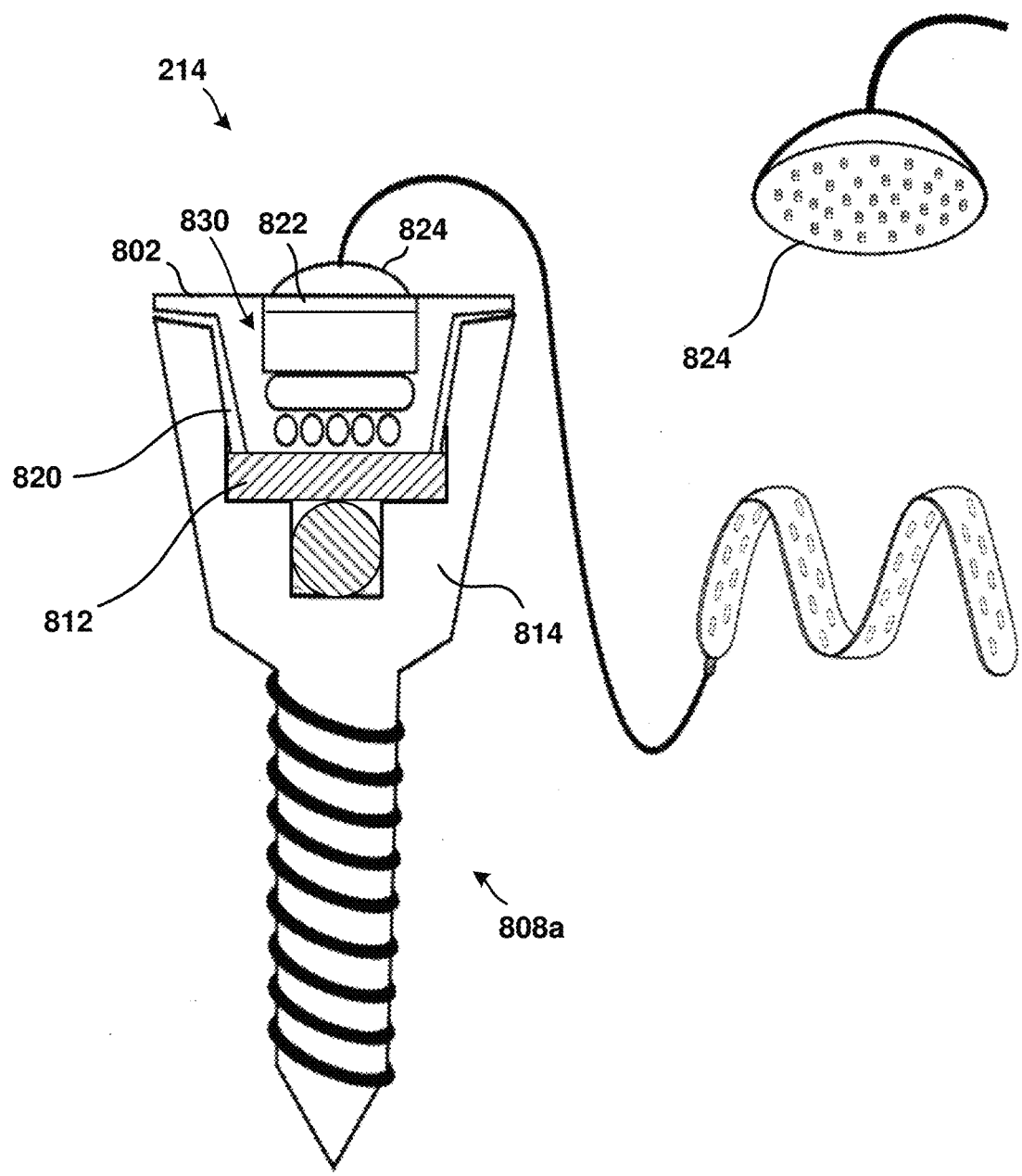
FIG. 8 is a schematic illustration of components of an alternate embodiment of a pain management system including a pedicle screw, a therapy module coupled to the screw-head of the pedicle screw, and a ribbon lead.

With reference to FIG. 8, in another alternate embodiment of a therapy module 214 configured for use with a pedicle screw 808a similar to the pedicle screw of FIG. 7, most of the electronic components 830 are located in a portion of the housing 802 that lies within the screw-head cavity 820 just above the threaded insert 812. The therapy module 214 may be coupled and decoupled from the screw-head 814 in anyone of the ways described above with reference to FIGS. 6A, 6B and 6C. The therapy module 214 includes an interface structure 822 comprising a plurality of electrical connectors exposed at the upper region of the housing 802. The electrical connectors are configured to mate with a corresponding plurality of electrical connectors of a lead interface structure 824.

Electronic Components

Figure 9:
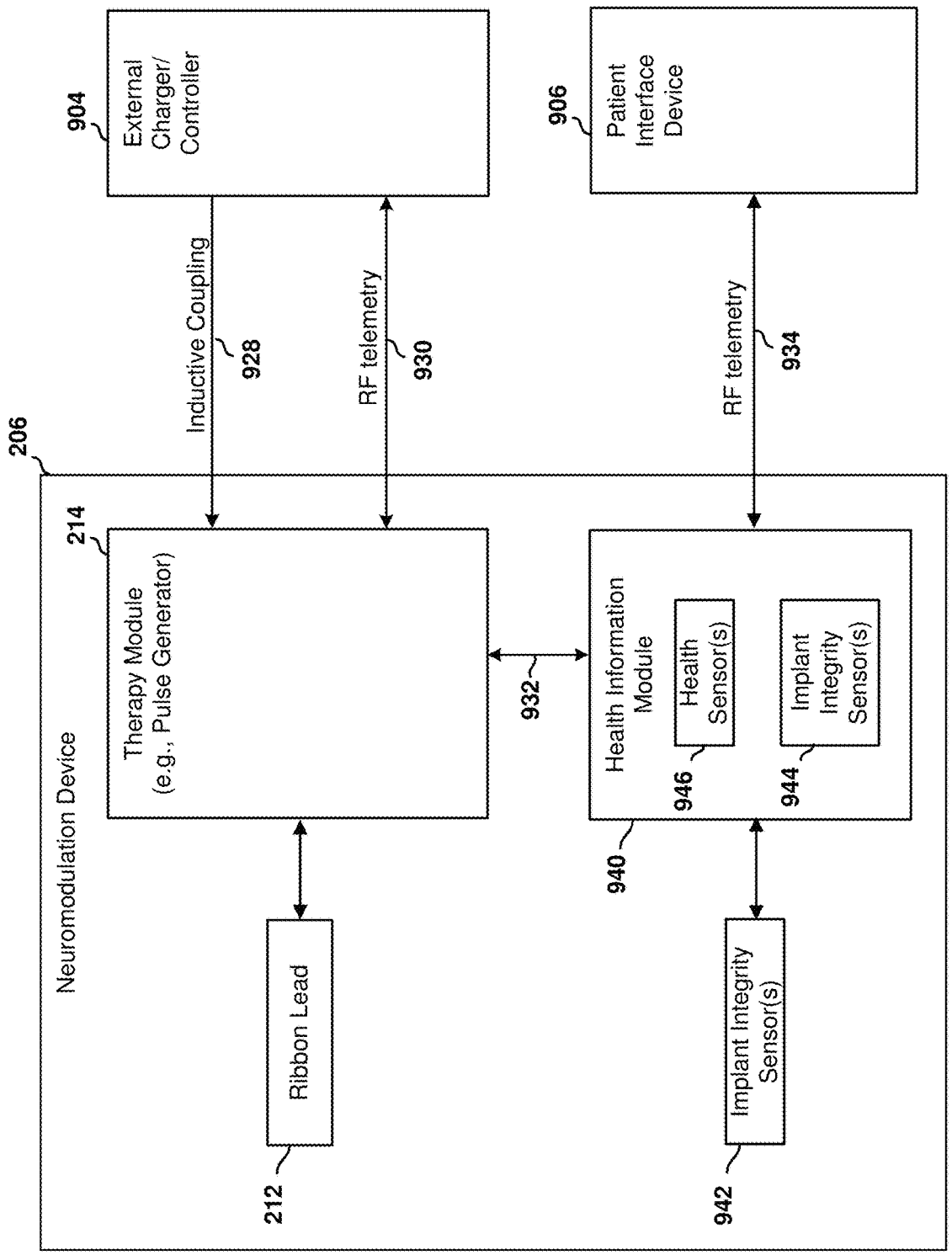
FIG. 9 is a block diagram of the system of FIG. 1A, including an implantable medical device comprising therapy module associated with one or more leads, a health information module associated with one or more sensors, and one or more external devices including an therapy controller and a patient interface device.

With reference to FIG. 9, the neuromodulation device 206 includes a therapy module 214 coupled to a ribbon lead 212 for delivering therapy to the patient. The neuromodulation device 206 may also include a health information module 940 associated with one or more implant-integrity sensors 942, 944 and one or more patient health sensors 946 for collecting and analyzing data, and indicating the condition of an orthopedic implant device and patient status. The implant-integrity sensors 942, 944 and patient health sensors 946 are typically included in the health information module. Some implant-integrity sensors, however, may be directly associated with the orthopedic implant device and coupled to the health information module 940 by a cable.

An external charger/controller 904 generates and transmits or emits energy to the therapy module through an inductive coupling 928. The therapy module 214 receives the energy transmitted by the charger/controller 904, stores the energy, and eventually uses the energy to generate and deliver a form of therapy to the patient through the ribbon lead 212. The inductive coupling between the charger/controller 904 and the therapy module 214 may also facilitate data communication between these components for the downloading of programming information from the charger/controller to the therapy module, and the uploading of operational information, e.g., therapy delivery records, from the therapy module to the charger/controller. Alternatively, programming and data collection between the therapy module 214 and the charger/controller 904 may be implemented through a wireless RF telemetry or Bluetooth interface 930. In either of the inductive coupling or the RF telemetry implementations, health information collected by the health information module 940 may also be uploaded to the charger/controller 904 through a communications bus 932 that interconnects the Therapy module 214 and the health information module.

An external patient interface device 906 may upload health information collected by the health information module 940 through a wireless RF telemetry or Bluetooth interface 934. Operational information, e.g., therapy delivery records, may also be uploaded to the external patient interface device 906 from the therapy module 214 through the communications bus 932 that interconnects the therapy module and the health information module 940. The external patient interface device 906 may also provide for limited operation control of the therapy module 214. To this end, the external patient interface device 906 may contain applications or software that would interact with the patient to assess his pain and adjust the stimulation parameters. The parameters could be adjusted manually by the patient, automatically by the therapy module in conjunction with the application algorithm, or remotely by the clinician. Command signals may be sent from the patient interface device to the therapy module 214 over the RF telemetry interface 934 and through the communication bus 932 to initiate the delivery of a therapy by the therapy module, or to program the therapy module to deliver a therapy in accordance with a therapy regimen.

Figure 10:
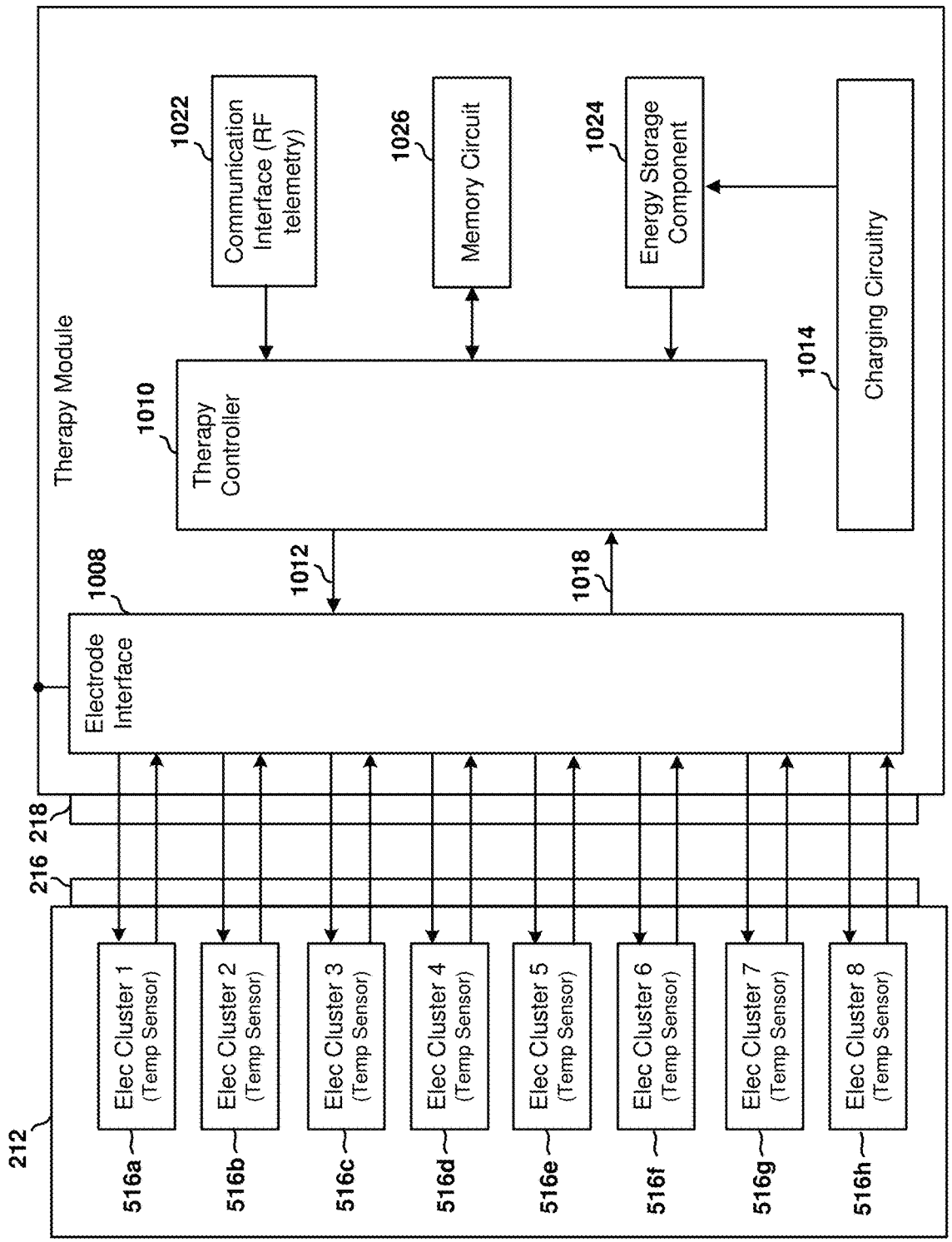
FIG. 10 is a block diagram of the therapy module and leads of FIG. 9.

FIG. 10 is a block diagram of the therapy module 214 and the ribbon lead 212 of FIG. 9. The therapy module 214 includes a therapy-module interface structure 218 adapted to interface with a corresponding lead interface structure 216 of the lead. The ribbon lead includes multiplexer circuitry for selecting one or more electrode cluster 516a-d, 516e-h to electrically interface with the electrode interface 1008. The electrode interface 1008, in turn, includes multiplexer circuitry for selecting one or more electrodes within the selected cluster as needed for delivery of a therapy. The electrode interface 1008 may also include circuitry that provides other features, or capabilities, including but not limited to isolation, and charge-balancing functions, that are required for a proper interface with neurological tissue.

The charging circuitry 1014 receives energy from the charger/controller 904 over the inductive coupling interface 928 and provides the energy to an energy storage component 1024 of the therapy module. The energy storage component 1024 may be a supercapacitor or one or more rechargeable batteries. In another configuration, energy may be provided by a remote inductive energy source and used in real time, in which case energy is note stores and the energy storage component 1024 may not be necessary.

A therapy controller 1010 is coupled to the electrode interface 1008 and controls the selection of electrodes by the electrode interface through control signals 1012. Electrode selection by the therapy controller 1010 may result in delivery of a therapy through a pair of electrodes in an electrode cluster 516*a-e*, 516*e-h*, e.g., a bipolar electrode configuration. The therapy module 214 also provides the signal needed to deliver electrical stimulation energy through the selected electrodes. The therapy controller 1010 is coupled to the energy storage component 1024 and configured to draw energy from the energy storage component and generate the stimulation energy signal.

Each electrode cluster 516*a-d*, 516*e-h* of the ribbon lead 212 may also include a temperature sensor configured to a provide signal indicative of the temperature at that cluster. The temperature sensors are coupled to the electrode interface 1008 through the lead interface structure 216 and therapy module interface structure 218. In one configuration, the temperature sensors provide a temperature feedback signal 1018 to the therapy controller 1010 to ensure that the temperature at the target area meets a specified criterion. Temperature feedback may also provide an indication of successful therapy settings. Related to heat as an alternate modality, the stimulation could also be used to generate a certain amount of non-damaging heat in the area that could be synergistically therapeutic.

In addition to supplying energy for the generation of therapy signals, the energy storage component 1024 supplies the voltages and currents necessary for operation of electronic components of the therapy module 214, including for example, components of the electrode interface 1008, the therapy controller 1010, and the charging circuitry 1014. The therapy module 214 also includes a memory circuit 1026. The memory circuit 1026 may store information corresponding to a history of delivered therapies, energy storage component recharge sessions, and temperature measurements.

The therapy module 214 may include a communications interface 1022 that enables RF telemetry communication between the therapy module and the charger/controller 904 through a wireless communication link. The charger/controller 904 allows a physician to program the therapy controller 1010 with a therapy regimen. For example, the therapy controller 1010 may be programmed to deliver periodic doses of a selected therapy during a treatment session. The communications interface 1022 also allows for the downloading of information from the memory circuit 1026.

Figure 11:
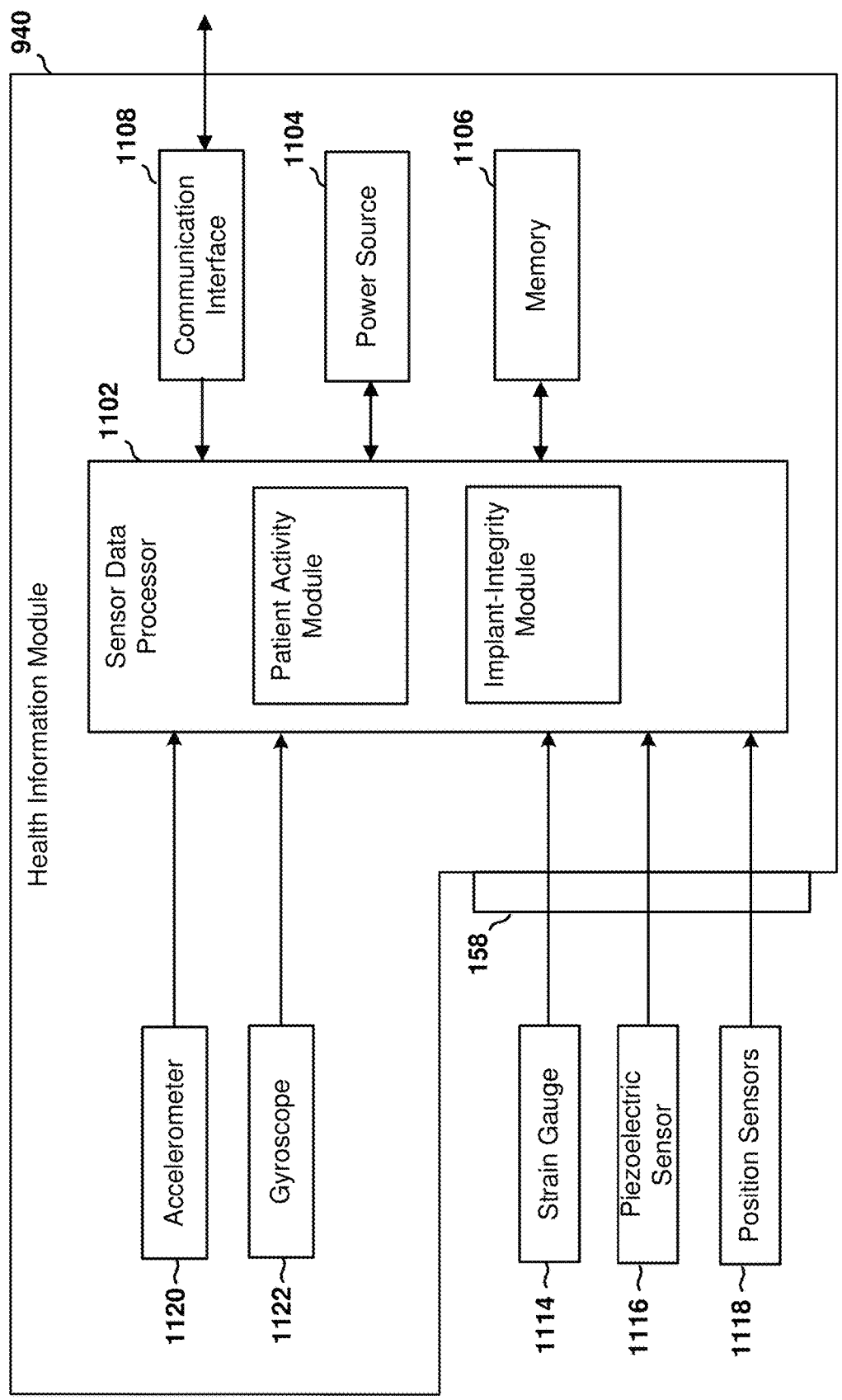
FIG. 11 is a block diagram of the health information module and associated sensors of FIG. 9.

FIG. 11 is a block diagram of the health information module 140 and various sensors 1114, 1116, 1118, 1120, 1122 that may function as one or both of an implant-integrity sensor and patient health sensors. The sensors include one or more strain gauges 1114, piezoelectric sensors 1116, position sensors/GPS 1118, each located remote from the health information module 140, and one or more accelerometers 1120 and gyroscopes 1122, each located within the information module. Sensors remote from the health information module 140 connect to a cable connector 158 or header of the module by cables. The cable connector 158 physically secures the cables to the health information module 140 and physically and electrically couples each sensor to a sensor data processor 1102 within the health information module 140.

The sensor data processor 1102 may obtain and process signals from the sensors 1114, 1116, 1118, 1120, 1122 to determine metrics indicative of the mechanical integrity of the implant device and/or patient heath. Alternatively, or in addition to, the external patient interface device 116 may obtain information from the health information module 140 and process the information to determine metrics. Several device-integrity metrics and patient-health metrics are envisioned, and the system 110 may be configured to determine one or more of these metrics.

A first device-integrity metric, referred to as a "load-bearing" metric, provides an indication of the load distribution among different hardware components of an orthopedic implant device. Most implant devices are configured so that after implant and after sufficient healing, the weight or force of the bone structure (herein referred to as "the load" of the bone structure) being applied to the implant device is distributed among hardware components of the device so that some components bear more of the load than other components. For example, in rod-and-screw spinal fixation device, the pedicle screws implanted in bone are intended to carry more load than the rod. A load distribution among hardware components that does not compart with the intended distribution may indicate that healing is not complete or that the implant device is not stable relative to the bone. Continuing with the rod-and-screw spinal fixation device, the device may become unstable or loose due to insufficient regrowth or fusion of boney material surrounding the pedicle screws. In this case, some of the load that would otherwise be carried by the pedicle screws would be redistributed to the rod.

A lead-bearing metric may be obtained, for example, through a strain gauge 1114 or piezoelectric sensor 1116 associated with a hardware component of the orthopedic implant device. The output of either of these sensors 1114, 1116 may serve as a measure of load carried by the component to which it is attached. Monitoring the output overtime allows for detection of changes in load that may correlate to reduced device integrity. For example, an increase in strain gauge 1114 output from a component that is not intended to carry as much load as another component indicates that the other component is loose. Again, continuing with the rod-and-screw spinal fixation device, an increase in output of a strain gauge 1114 attached to the rod indicates that the pedicle screws are loose.

A second device-integrity metric, referred to as a "relative-position" metric, provides an indication of the relative positions of different hardware components of an orthopedic implant device. Most implant devices are configured so that after implant and after sufficient healing, the positions of different hardware components of the device relative to each other are fixed. For example, in a rod-and-screw spinal fixation device, the relative positions of pedicle screws and the rod should be fixed. A relative position finding or metric among hardware components that does not compart with a fixed positioning may indicate that one or both of the hardware components is not stable. Continuing with the rod-and-screw spinal fixation device, the device may become unstable or loose due to insufficient regrowth or fusion of boney material surrounding the pedicle screws. In this case, the relative position between the pedicle screws and rod would change from a baseline value.

A relative position metric may be obtained, for example, through position sensors 1118, such as GPS sensors, that are associated with hardware components of the orthopedic implant device. The output of the position sensors 1118 may serve as a measure of distance between the two components. Monitoring the output overtime allows for detection of changes in distance that may correlate to reduced device integrity. For example, an increase in distance indicates that the hardware components have moved relative to each other. Again, continuing with the rod-and-screw spinal fixation device, an increase in the distance between the rod and either of the pedicle screws indicates that one of the hardware components has moved and may be loose.

A third device-integrity metric, referred to as a "stability" metric, provides an indication of the stability of one or more hardware components of an orthopedic implant device. Implant devices are configured so that after implant and after sufficient healing, the different hardware components of the device are fixed in place. For example, in the rod-and-screw spinal fixation device, the pedicle screws and the rod should be fixed. A stability metric for a hardware component that does not compart with that of stable and fixed position may indicate that one or both of the hardware components is loose. Continuing with the rod-and-screw spinal fixation device, the device may become unstable or loose due to insufficient regrowth or fusion of boney material surrounding the pedicle screws.

A stability metric may be obtained, for example, through an accelerometer 1120 within the health information module 140. The accelerometer 1120 senses motion and vibration and outputs signals representing such movements. Some movements may be due to patient activity, while other movements may be due to movement of a hardware component. For example, a loose pedicle screw may lead to vibration of the rod which in turn would result in vibration of the health information module 140 secured to the rod. The sensor data processor 1102 within the health information module 140 may process the signals to distinguish between movement due to the patient from movement due to the implant device. This may be done through filtering and spectral analysis of the accelerometer signal, wherein movement resulting from vibration of the rod is at a different spectral frequency component that that caused by patient movement.

A first patient-heath metric, referred to herein as an "activity" metric provides an indication of the movement of the patient. An activity metric may be obtained, for example, through the accelerometer 1120 in the health information module 140. As just noted, the accelerometer 1120 senses motion and vibration and outputs signals representing such movements. Some movements may be due to patient activity, while other movements may be due to movement of a hardware component. The sensor data processor 1102 within the health information module 140 may process the signals to distinguish between movement due to the patient from movement due to the implant device. This may be done through filtering and spectral analysis of the accelerometer signal, wherein movement resulting from vibration of the rod is at a different spectral frequency component that that caused by patient movement. Potential biomarkers for pain and or successful relief of pain may be indicated by patient movement, posture, exercise/activity and amount of movement in the environment (i.e. going out/travel).

A second patient-heath metric, referred to herein as a "motion" metric provides an indication of the range of motion of the patient. For example, this metric may indicate a patient's ability to bend over, or turn in a certain direction. A motion metric may be obtained, for example, through a gyroscope 1122 in the health information module 140.

In addition to the various sensors, the health information module 140 includes a power source 1104, a memory circuit 1106 and a communication interface 1108. The power source 1104 supplies the voltages and currents necessary for operation of electronic components of the module, including for example, components of the sensor data processor 1102, the sensors and the communication interface 1108. The power source 1104 may be configured to be recharged through an inductive coupling link like the one described above with reference to the therapy module 114. The memory circuit 1106 may store information corresponding to a history of sensor outputs and metrics determined by the sensor data processor 1102.

The communications interface 1108 enables RF telemetry communication between the health information module and the external patient interface device 116 through a wireless communication link. The external patient interface device 116 allows for the downloading of information from the memory circuit 1106. Information may also be downloaded from the memory circuit 1106 through the inductive coupling link by inductive telemetry when the interface is not being used for charging purposes.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An implantable neuromodulation device for implant with a spinal stabilization device that includes a pair of pedicle screws, a rod, and a pair of inserts, each insert configured to secure a portion of the rod in a screw-head cavity of a screw-head of one of the pedicle screws, the neuromodulation device comprising:
 a therapy module comprising a housing having a form factor comprising at least one feature configured to mate with a corresponding feature of the screw-head of one of the pedicle screws, wherein the respective features mate in a manner that enables the therapy module to mechanically couple to and subsequently decouple from the screw-head of the pedicle screw; and
 a lead comprising a distal-end region having a plurality of electrodes and a proximal-end region having a lead interface structure configured to mechanically and electrically couple to and subsequently decouple from the therapy module.

2. The neuromodulation device of claim 1, wherein:
the at least one feature of the housing comprises a center projection having an outer wall;
the corresponding feature of the screw-head comprises the screw-head cavity;
the center projection mates with the screw-head cavity through one of: a threaded engagement between the outer wall of the center projection and one or more inner walls of the cavity, and a friction fit between the outer wall of the projection and one or more inner walls of the cavity.

3. The neuromodulation device of claim 2, wherein:
the at least one feature of the housing comprises a pair of opposed side projections defining a housing cavity;
the corresponding feature of the screw-head comprises the screw-head itself;
the screw-head mates with the housing cavity through one of: a threaded engagement between the outer wall of the screw-head and one or more inner walls of the opposed side projections, and a friction fit between the outer wall of the screw-head and one or more inner walls of the opposed side projections.

4. The neuromodulation device of claim 3, wherein the therapy module comprises a therapy-module interface structure configured to couple with the lead interface structure.

5. The neuromodulation device of claim 4, wherein the therapy-module interface structure comprises a dongle having at least one in-line connector configured to mate with a corresponding connector of the lead interface structure.

6. The neuromodulation device of claim 4, wherein the housing comprises an upper region, and the therapy-module interface structure comprises a plurality of electrical contacts exposed at the upper region and configured to mate with a corresponding plurality of electrical contacts of the lead interface structure.

7. The neuromodulation device of claim 1, wherein the housing comprises a groove formed in a pliable surface of the housing, the groove configured to receive a portion of the lead body and secure the portion in place through a friction fit.

8. A pain management system comprising:
a spinal stabilization device comprising a rod, a plurality of pedicle screws each having a screw-head defining a screw-head cavity configured to receive a portion of the rod, and a corresponding plurality of inserts configured to engage with the inner wall of the cavity to secure the rod in place in the cavity; and
a neuromodulation device comprising a therapy module comprising electronics packaged within a housing having a form factor comprising at least one feature configured to mate with a corresponding feature of the screw-head of one of the plurality of pedicle screws, wherein the respective features mate in a manner that enables the therapy module to mechanically couple to and subsequently decouple from the screw-head of the pedicle screw.

9. The pain management system of claim 8, further comprising an implantable medical lead comprising a ribbon structure having a plurality of electrodes and a lead interface structure configured to mechanically and electrically couple to and subsequently decouple from the therapy module.

10. The pain management system of claim 8, further comprising an implantable medical lead comprising:
a ribbon structure having a first side and a second side opposite the first side;
a plurality of first electrodes associated with the first side and arranged in a first pattern; and
a plurality of second electrodes associated with the second side and arranged in a second pattern;
wherein the ribbon structure is configured to transition from a planar state to a non-planar state upon the application of a force and to remain in the non-planar state upon removal of the force.

11. A method of implanting a pain management system that includes spinal stabilization hardware and a neuromodulation device having a therapy module configured to mechanically couple to and decouple from a component of the spinal stabilization hardware, the method comprising:
creating direct access to nerve structures while implanting the spinal stabilization hardware during a spinal fusion procedure;
placing a lead on or adjacent to target nerve structures under direct visual access;
mechanically coupling the therapy module to a component of the spinal stabilization hardware; and
mechanically and electrically coupling the lead to the therapy module.

* * * * *